(12) United States Patent
Trezza, II et al.

(10) Patent No.: US 12,207,810 B2
(45) Date of Patent: Jan. 28, 2025

(54) DISPENSING SYSTEMS AND DEVICES HAVING ANTI-CLOGGING SPRAY TIPS FOR DISPENSING TWO OR MORE FLUIDS THAT REACT TOGETHER

(71) Applicant: Ethicon, Inc., Somerville, NJ (US)

(72) Inventors: Michael J. Trezza, II, Long Valley, NJ (US); Salim A. Ghodbane, Piscataway, NJ (US); Jianxin Guo, Livingston, NJ (US)

(73) Assignee: Ethicon, Inc., Somerville, NJ (US)

( * ) Notice: Subject to any disclaimer, the term of this patent is extended or adjusted under 35 U.S.C. 154(b) by 887 days.

(21) Appl. No.: 16/593,783

(22) Filed: Oct. 4, 2019

(65) Prior Publication Data

US 2021/0100543 A1    Apr. 8, 2021

(51) Int. Cl.
*A61B 17/00* (2006.01)
*A61M 5/19* (2006.01)
*A61M 5/31* (2006.01)

(52) U.S. Cl.
CPC ......... *A61B 17/00491* (2013.01); *A61M 5/19* (2013.01); *A61M 5/31* (2013.01);
(Continued)

(58) Field of Classification Search
CPC .... A61B 17/00491; A61B 2017/00495; A61B 2017/00522; A61B 2017/0065; A61M 2206/12
See application file for complete search history.

(56) References Cited

U.S. PATENT DOCUMENTS

| 4,846,405 A | 7/1989 | Zimmermann |
| 4,981,241 A * | 1/1991 | Keller ...................... A61C 5/64 |
| | | 222/137 |

(Continued)

FOREIGN PATENT DOCUMENTS

| EP | 2158848 | 3/2010 |
| JP | 2002282368 | 10/2002 |

(Continued)

OTHER PUBLICATIONS

Blasterparts: "NERF—Super Soaker FlashFlood," www.blasterparts.com/en/p/nerf-super-soaker-flashflood--560280, Jul. 13, 2019, pp. 1-6.

(Continued)

*Primary Examiner* — Diane D Yabut
*Assistant Examiner* — Christian D Knauss
(74) *Attorney, Agent, or Firm* — Troutman Sanders Hamilton Sanders LLP

(57) ABSTRACT

A spray tip for dispensing fluids that react together includes a first lumen for a first fluid, a second lumen for a second fluid, and a dispensing cap located at distal ends of the respective first and second lumens and defining a distal end of the spray tip. The dispensing cap includes a distal end wall defining a closed end of the dispensing cap, a first spray opening formed in the distal end wall that is in fluid communication with the first lumen, a second spray opening formed in the distal end wall that is in fluid communication with the second lumen, and an external dividing wall that projects distally from the distal end wall of the dispensing cap and that extends between the first and second spray opening for forming a barrier between the first and second spray openings.

22 Claims, 24 Drawing Sheets

(52) U.S. Cl.
CPC .............. *A61B 2017/00495* (2013.01); *A61B 2017/00522* (2013.01); *A61M 2005/3128* (2013.01); *A61M 2206/12* (2013.01)

(56) References Cited

U.S. PATENT DOCUMENTS

| | | | |
|---|---|---|---|
| 5,152,460 | A | 10/1992 | Barty |
| 5,368,563 | A | 11/1994 | Lonneman et al. |
| 5,526,981 | A | 6/1996 | Sanson |
| 5,759,169 | A | 6/1998 | Marx |
| 6,432,084 | B1 | 8/2002 | Levinson et al. |
| 6,547,161 | B1 | 4/2003 | Huang |
| 6,612,506 | B1 | 9/2003 | Huang |
| 6,835,186 | B1 * | 12/2004 | Pennington ............ A61L 31/046 604/82 |
| 7,163,160 | B2 | 1/2007 | Liu |
| 7,694,944 | B2 | 4/2010 | Gottlieb et al. |
| 8,033,483 | B2 | 10/2011 | Fortier et al. |
| 8,408,480 | B2 | 4/2013 | Hull et al. |
| 2003/0069537 | A1 | 4/2003 | Spero et al. |
| 2006/0189944 | A1 * | 8/2006 | Campbell ........ A61B 17/00491 604/191 |
| 2006/0253082 | A1 | 11/2006 | McIntosh et al. |
| 2008/0272209 | A1 * | 11/2008 | Yokoyama ............ B05B 7/1281 239/10 |
| 2009/0108091 | A1 | 4/2009 | Steffan |
| 2011/0245866 | A1 * | 10/2011 | Cassingham .... A61B 17/00491 606/213 |
| 2011/0253806 | A1 * | 10/2011 | Brem ................ B01F 33/50112 239/549 |
| 2011/0319930 | A1 * | 12/2011 | Roush .................. B01F 35/522 606/213 |
| 2013/0325059 | A1 | 12/2013 | O'Neill |
| 2016/0067423 | A1 | 3/2016 | Goodman et al. |
| 2016/0354803 | A1 | 12/2016 | Smith |
| 2018/0177978 | A1 | 6/2018 | Spivey et al. |
| 2019/0029660 | A1 | 1/2019 | Hull et al. |
| 2020/0139385 | A1 * | 5/2020 | Hartranft ............. B65D 83/753 |

FOREIGN PATENT DOCUMENTS

| | | |
|---|---|---|
| JP | 2007090347 A | 12/2006 |
| JP | 2009291598 A | 12/2009 |

OTHER PUBLICATIONS

Tamer, et al., "Fibrin: A Versatile Scaffold for Tissue Engineering Applications," Tissue Engineering Part B—Reviews, Jun. 1, 2008, p. 203, Figure 3, vol. 14, No. 2, Publisher—Mary Ann Liebert, Inc., US.

"FibriJet Biomaterial Delivery Devices," Nordson Medical, St. Paul, MN, https://www.nordsonmedical.com/Components-and-Technologies/Biomaterial-Delivery-Devices/FibriJet-Delivery-Devices/, a copy of the submitted document was obtained on Nov. 6, 2019 from the website www.nordsonmedical.com (no publication date is provided on the document), 32 pages.

International Search Report issued in corresponding International Application No. PCT/IB2020/059226, mailed on Dec. 16, 2020.

"FibriJet Biomaterial Delivery Devices," Nordson Medical, St. Paul, MN, www.nordsonmedical.com, 32 pages.

"Rely on EVICEL Fibrin Sealant," Ethicon US, LLC, 2015, 6 pages.

English translation of Search Report dated Mar. 15, 2024, from corresponding Japanese Application No. 2022-520466.

English translation of Notice of Reasons for Refusal dated Mar. 19, 2024, from corresponding Japanese Application No. 2022-520466.

English translation of Decision to Grant a Patent dated Jul. 9, 2024, from corresponding Japanese Application No. 2022-520466.

* cited by examiner

DISPENSING SYSTEMS AND DEVICES HAVING ANTI-CLOGGING SPRAY TIPS FOR DISPENSING TWO OR MORE FLUIDS THAT REACT TOGETHER

BACKGROUND OF THE INVENTION

Field of the Invention

The present patent application is generally related to medical devices for dispensing fluids, and is more specifically related to fluid dispensing systems having spray tips that dispense fluids used in medical and surgical procedures.

Description of the Related Art

Recently, minimally invasive surgery (MIS) techniques have emerged as an alternative to conventional surgical techniques for performing a wide range of surgical procedures. MIS procedures differ from conventional surgical procedures in that a plurality of devices and/or surgical tools may be introduced into the body through cannulas and trocars that are inserted into small incisions. As a result, trauma to the body is greatly reduced, thereby decreasing the recovery time for patients.

One type of minimally invasive surgery involves laparoscopic surgical procedures, which are used to treat hernias, colon dysfunctions, gastroesophageal reflux disease, gallbladder disorders, etc. Typically, a patient undergoing a laparoscopic surgical procedure is able to return home within hours after undergoing surgery.

One challenge presented when performing minimally invasive surgical procedures relates to controlling bleeding at the surgical site. In contrast to conventional open surgical procedures, during a laparoscopic procedure a surgeon's access to a surgical site or surgical cavity is greatly reduced.

In response, the use of tissue sealants and other biological adhesive materials has emerged as a technique for closing incisions at surgical sites. Tissue sealants may include fibrin sealants, which is comprised of thrombin, and a fibrinogen material, although other formulations are also available. Typically, the individual components of the tissue sealants are stored separately in isolated reservoirs. The components are mixed together for the first time immediately prior to being applied to tissue. Once mixed, the components coagulate very quickly, yielding an adhesive gel within a short period of time (e.g., within 10-20 seconds). When considerable access to the application site is possible, the rapid coagulative properties of the tissue sealant are advantageous. However, the fast-acting properties of tissue sealants often clog the spray tips that are used for dispensing the components.

In addition, it is difficult to manufacture flexible accessories for delivering a two component material to a location in vivo. The components of the material are stored separately in and expressed out of a dual syringe, which requires a minimum distance between the exit orifices of the dual syringe. To be functional, the flexible cannula must be significantly smaller than the minimum distance between the exit orifices of the dual syringe, which results in two physically separated fluid paths coming together to fit through a cannula or trocar.

Various devices for spraying fluids are disclosed in U.S. Pat. Nos. 7,694,944, 5,152,460, 6,547,161, 6,612,506, 5,526,981, and 7,163,160.

Medical devices for spraying at least two fluid components that react together rapidly are disclosed in U.S. Pat. No. 6,432,084, and U.S. Patent Application Publication No. 2009/0108091. The above-identified documents, however, are silent regarding the performance of the medical devices when spraying is carried out in close proximity to the target location.

Commercially available spray tips that are used to atomize tissue sealants typically operate by mixing the components of the tissue sealant inside the spray tip and prior to spraying. Due to the quick acting nature of the biologics, the spray tips typically clog as soon as the flow of fluid through the spray tip stops (e.g., typically within one to two seconds). Once the spray tips become clogged, they can no longer be used to atomize biologics and must be replaced with new spray tips.

In view of the above-noted deficiencies, there is a need for dispensing devices having spray tips that provide surgeons with the ability to spray biologics and quick-acting tissue sealants, evaluate the results of the spray (e.g., has hemostasis occurred?), and then continue spraying without the need for changing spray tips. Satisfying this need is particularly valuable in minimally invasive/robotic surgery where removing the device to change the spray tip and reposition the device for spraying is a more time-consuming procedure.

Moreover, there is a need for improved anti-clogging spray tips for dispensing tissue sealants onto tissue.

In addition, there is a need for a medical device for spraying two components, which react together rapidly, in close proximity to a target surface.

There is also a need for a device capable of effectively delivering a multiple component tissue sealant to a location in vivo from a remote location, whereby the device may be easily and reproducibly manufactured.

SUMMARY OF THE INVENTION

In one embodiment, a spray tip for dispensing fluids that react together preferably includes a first lumen for a first fluid, a second lumen for a second fluid, and a dispensing cap located at distal ends of the respective first and second lumens, which desirably defines a distal end of the spray tip. In one embodiment, the first and second lumens adapted to receive the components (e.g., a first fluid and a second fluid) of a tissue sealant and/or other biological adhesive materials. In one embodiment, the tissue sealants and/or other biologic adhesive materials are preferably used for controlling bleeding at surgical sites. In one embodiment, the tissue sealants may include a fibrin sealant, which is comprised of thrombin, and a fibrinogen material, although other formulations may also be used.

In one embodiment, the dispensing cap preferably includes a distal end wall defining a closed end of the dispensing cap, a first spray orifice formed in the distal end wall that is in fluid communication with the first lumen, and a second spray orifice formed in the distal end wall that is in fluid communication with the second lumen. In one embodiment, the dispensing cap desirably includes an external dividing wall that projects distally from a distal face of the distal end wall of the dispensing cap and that extends between the first and second spray orifices for forming a barrier between the first and second spray orifices. The external dividing wall preferably prevents the components of a tissue sealant (e.g., Fibrinogen and Thrombin) from contacting one another on an outer surface of the dispensing cap, which could result in clogging of one or one of the first and second spray orifices. In one embodiment, the components of a tissue sealant are mixed together for the first time only after being sprayed from the first and second spray orifices and flowing distally beyond the distal end of the external dividing wall.

In one embodiment, the first spray orifices preferably includes a first raised mound that projects distally from the distal face of the distal end wall of the dispensing cap. A first spray opening may be provided in the first raised mound. In one embodiment, the second spray orifice preferably includes a second raised mound that projects distally from the distal face of the distal end wall of the dispensing cap. A second spray opening may be provided in the second raised mound. In one embodiment, the external dividing wall has a proximal end that is secured to the distal face of the distal end wall and a distal, free end that is distal to respective apexes of the first and second raised mounds for defining a distal-most end of the dispensing cap.

In one embodiment, the first and second raised mounds of the respective first and second spray orifices may include hydrophobic surfaces that are adapted for repelling fluids that contact the first and second raised mounds, which preferably minimizes the likelihood of fluids pooling over the outer surfaces of the spray orifices for preventing clogging of the spray orifices.

In one embodiment, the dispensing cap preferably includes a cylindrical shaped body having a proximal end that is open for coupling with the distal ends of the first and second lumens and a distal end that is closed by the distal end wall.

In one embodiment, the dispensing cap may includes an internal dividing wall located inside the cylindrical shaped body that extends between the proximal end of the cylindrical shaped body and the distal end wall for dividing an interior region of the dispensing cap into a first chamber that is in fluid communication with the first lumen and a second chamber that is in fluid communication with the second lumen.

In one embodiment, the distal end wall of the dispensing cap desirably has an inner surface, and the internal dividing wall has a distal end that is secured to the inner surface of the distal end wall for dividing the inner surface of the distal end wall of the dispensing cap into a first region that is disposed within the first chamber and a second region that is disposed within the second chamber.

In one embodiment, the spray tip preferably includes a first fluid pathway formed in the first region of the inner surface of the distal end wall of the dispensing cap. The first fluid pathway is desirably in fluid communication with the first spray orifice.

In one embodiment, the spray tip preferably includes a second fluid pathway formed in the second region of the inner surface of the distal end wall of the dispensing cap. The second fluid pathway desirably is in fluid communication with the second spray orifice.

In one embodiment, the first fluid pathway may include a first swirl chamber that is in fluid communication with the first spray orifice, and a pair of first flutes that extend radially outward from the first swirl chamber. In one embodiment, each of the first flutes has a width that may narrow between outer and inner ends thereof.

In one embodiment, the second fluid pathway may include a second swirl chamber that is in fluid communication with the second spray orifice, and a pair of second flutes that extend radially outward from the second swirl chamber. In one embodiment, each of the second flutes has a width that may narrow between outer and inner ends thereof.

In one embodiment, the first lumen may contain a first fluid that is directed into the first fluid pathway of the dispensing cap. In one embodiment, the first swirl chamber of the first fluid pathway is configured to rotate the first fluid prior to dispensing (e.g., spraying) the first fluid from the first spray orifice.

In one embodiment, the second lumen may contain a second fluid that is directed into the second fluid pathway of the dispensing cap. In one embodiment, the second swirl chamber of the second fluid pathway is configured to rotate the second fluid prior to dispensing (e.g., spraying) the second fluid from the first spray orifice.

In one embodiment, the first and second fluids chemically react together after being dispensed (e.g., sprayed) from the respective first and second spray orifices. In one embodiment, the external, distally extending dividing wall preferably serves as a barrier that separates the first and second fluids from one another until the fluids move distally beyond the distal end of the dividing wall.

In one embodiment, the first flutes extend away from one another on opposite sides of the first swirl chamber, and the second flutes extend away from one another on opposite sides of the second swirl chamber.

In one embodiment, a spray tip for spraying a tissue sealant preferably has multiple orifices (e.g., two spray openings) for spraying the components of the tissue sealant. In one embodiment, each biologic/reactant component is preferably dispensed through only one of the spray orifices to prevent clotting from occurring before the fluids are dispensed through the respective spray orifices, thereby preventing the formation of clogs and/or blockages in the spray tip.

In one embodiment, a spray tip for spraying a tissue sealant preferably includes a dividing wall that is positioned between the spray orifices. The dividing wall preferably prevents the biologics/reactants that are on the surfaces of the spray tip from contacting each other and reacting, which could clog the spray tip. The dividing wall is preferably an external dividing wall that extends distally from a distal end of the spray tip.

In one embodiment, the spray orifices preferably includes raised openings (e.g., raised mounds), which allow biologics/reactants on the surfaces of the spray orifices to run off of the surfaces of the spray orifices for preventing any potential surface clots and/or clogs from forming over the spray openings.

In one embodiment, a dispensing device for the spray tip preferably includes a one way/check valve associated with each lumen for each biologic/reactant component. The one-way check valves preferably prevent back flow of the components of the tissue sealant. For example, during back flow, the biologics/reactants present on the spray tip could be sucked back into the spray openings, which may result in clogged spray openings.

In one embodiment, the spray tip preferably includes one or more hydrophobic surfaces, which minimize the likelihood of biologics/reactants remaining on critical surfaces (e.g., the spray orifices), thereby reducing the occurrence of surface clots and/or clogging of the spray orifices.

In one embodiment, a spray tip for dispensing fluids that react together preferably includes a first lumen for a first fluid, a second lumen for a second fluid, and a dispensing cap located at distal ends of the respective first and second lumens. In one embodiment, the dispensing cap desirably includes a cylindrical shaped body having a proximal end that is open for receiving distal ends of the first and second lumens and a distal end that is closed by a distal end wall.

In one embodiment, the dispensing cap may include a first spray orifice formed in the distal end wall that is in fluid communication with the first lumen, whereby the first spray orifice includes a first raised mound that projects distally from an outer surface of the distal end wall of the dispensing cap.

In one embodiment, the dispensing cap may include a second spray orifice formed in the distal end wall that is in fluid communication with the second lumen, whereby the second spray orifice includes a second raised mound that projects distally from the outer surface of the distal end wall of the dispensing cap.

In one embodiment, the dispensing cap preferably has an external dividing wall that projects distally from the outer surface of the distal end wall of the dispensing cap. In one embodiment, the external dividing wall preferably extends between the first and second spray orifices for forming a barrier between the first and second spray orifices at the outer surface of the distal end wall of the dispensing cap.

In one embodiment, the dispensing cap may include an internal dividing wall located inside the cylindrical shaped body that extends between the proximal end of the cylindrical shaped body and an interior surface of the distal end wall for dividing an interior region of the dispensing cap into a first chamber that is in fluid communication with the distal end of the first lumen and a second chamber that is in fluid communication with the distal end of the second lumen.

In one embodiment, the spray tip may include a first fluid pathway formed in the first region of the inner surface of the distal end wall of the dispensing cap. In one embodiment, the first fluid pathway is in fluid communication with the distal end of the first lumen and the first spray opening.

In one embodiment, the spray tip may include a second fluid pathway formed in the second region of the inner surface of the distal end wall of the dispensing cap. In one embodiment, the second fluid pathway is in fluid communication with the distal end of the second lumen and the second spray opening.

In one embodiment, the first fluid pathway desirably includes a first swirl chamber that is formed in the inner surface of the distal end wall and that is in fluid communication with the first spray opening, and a pair of first flutes that are formed in the inner surface of the distal end wall and that extend radially outward from the first swirl chamber to an outer perimeter of the inner surface of the distal end wall of the dispensing cap. In one embodiment, each of the first flutes has a width. In one embodiment, the widths of the first flutes may narrow between the respective outer and inner ends thereof.

In one embodiment, the second fluid pathway desirably includes a second swirl chamber that is formed in the inner surface of the distal end wall and that is in fluid communication with the second spray opening, and a pair of second flutes that are formed in the inner surface of the distal end wall and that extend radially outward from the second swirl chamber to an outer perimeter of the inner surface of the distal end wall of the dispensing cap. In one embodiment, each of the second flutes has a width. In one embodiment, the widths of the second flutes may narrow between the respective outer and inner ends thereof.

In one embodiment, the external dividing wall has a proximal end that is secured to a distal face or outer surface of the distal end wall and a distal, free end that is distal to the respective apexes of the first and second raised mounds for defining a distal-most end of the dispensing cap.

In one embodiment, a spray tip for dispensing fluids that react together preferably includes a first lumen for a first fluid, a second lumen for a second fluid, and a dispensing cap located at distal ends of the first and second lumens.

In one embodiment, the dispensing cap preferably includes a cylindrical shaped body having a proximal end that is open for being coupled with the distal ends of the first and second lumens and a distal end that is closed by a distal end wall having an inner surface and an outer surface/distal face.

In one embodiment, the dispensing cap may include a first spray orifice formed in the distal end wall that is in fluid communication with the distal end of the first lumen. In one embodiment, the first spray orifice preferably includes a first raised mound that projects distally from the outer surface of the distal end wall of the dispensing cap.

In one embodiment, the dispensing cap may include a second spray orifice formed in the distal end wall that is in fluid communication with the distal end of the second lumen. In one embodiment, the second spray orifice preferably includes a second raised mound that projects distally from the outer surface of the distal end wall of the dispensing cap.

In one embodiment, the dispensing cap desirably includes an external dividing wall that projects distally from the outer surface/distal face of the distal end wall of the dispensing cap. In one embodiment, the dividing wall preferably extends across the outer surface/distal face of the distal end wall of the dispensing cap and between the first and second spray orifices for forming a barrier between the first and second spray orifices.

In one embodiment, the dispensing cap desirably includes the cylindrical shaped body having a cylindrical shaped wall that extends from the proximal end to the distal end of the cylindrical shaped body. In one embodiment, the dispensing cap preferably includes an internal dividing wall located inside the cylindrical shaped body that divides the cylindrical shaped body into two parts. In one embodiment, the internal dividing wall preferably extends between the proximal end of the cylindrical shaped body and the inner surface of the distal end wall for dividing the inner surface of the distal end wall into a first region that is in fluid communication with the distal end of the first lumen and a second region that is in fluid communication with the distal end of the second lumen.

In one embodiment, the dispensing cap preferably includes a first fluid pathway formed in the first region of the inner surface of the distal end wall of the dispensing cap. In one embodiment, the first fluid pathway is desirably located between the distal end of the first lumen and the first spray orifice.

In one embodiment, the dispensing cap desirably includes a second fluid pathway formed in the second region of the inner surface of the distal end wall of the dispensing cap. In one embodiment, the second fluid pathway is desirably located between the distal end of the second lumen and the second spray orifice.

In one embodiment, the first fluid pathway preferably includes a first swirl chamber formed in the inner surface of the distal end wall that is in fluid communication with the first spray orifice, and a pair of first flutes that are formed in the inner surface of the distal end wall and that extend radially outward from the first swirl chamber.

In one embodiment, the second fluid pathway desirably includes a second swirl chamber formed in the inner surface of the distal end wall that is in fluid communication with the second spray orifice, and a pair of second flutes that are formed in the inner surface of the distal end wall and that extend radially outward from the first swirl chamber.

These and other preferred embodiments of the present invention will be described in more detail below.

BRIEF DESCRIPTION OF THE DRAWINGS

FIG. 8B-1 is a magnified view of the first fluid pathway shown in FIG. 8A.

FIG. 8B-2 is a perspective view of the first fluid pathway shown in FIG. 8A.

FIG. 8B-3 is a cross-sectional view of the first fluid pathway shown in FIG. 8A.

FIG. 8B-4 is a perspective cross-sectional view of the first fluid pathway shown in FIG. 8A.

DETAILED DESCRIPTION OF PREFERRED EMBODIMENTS

Figure 1:
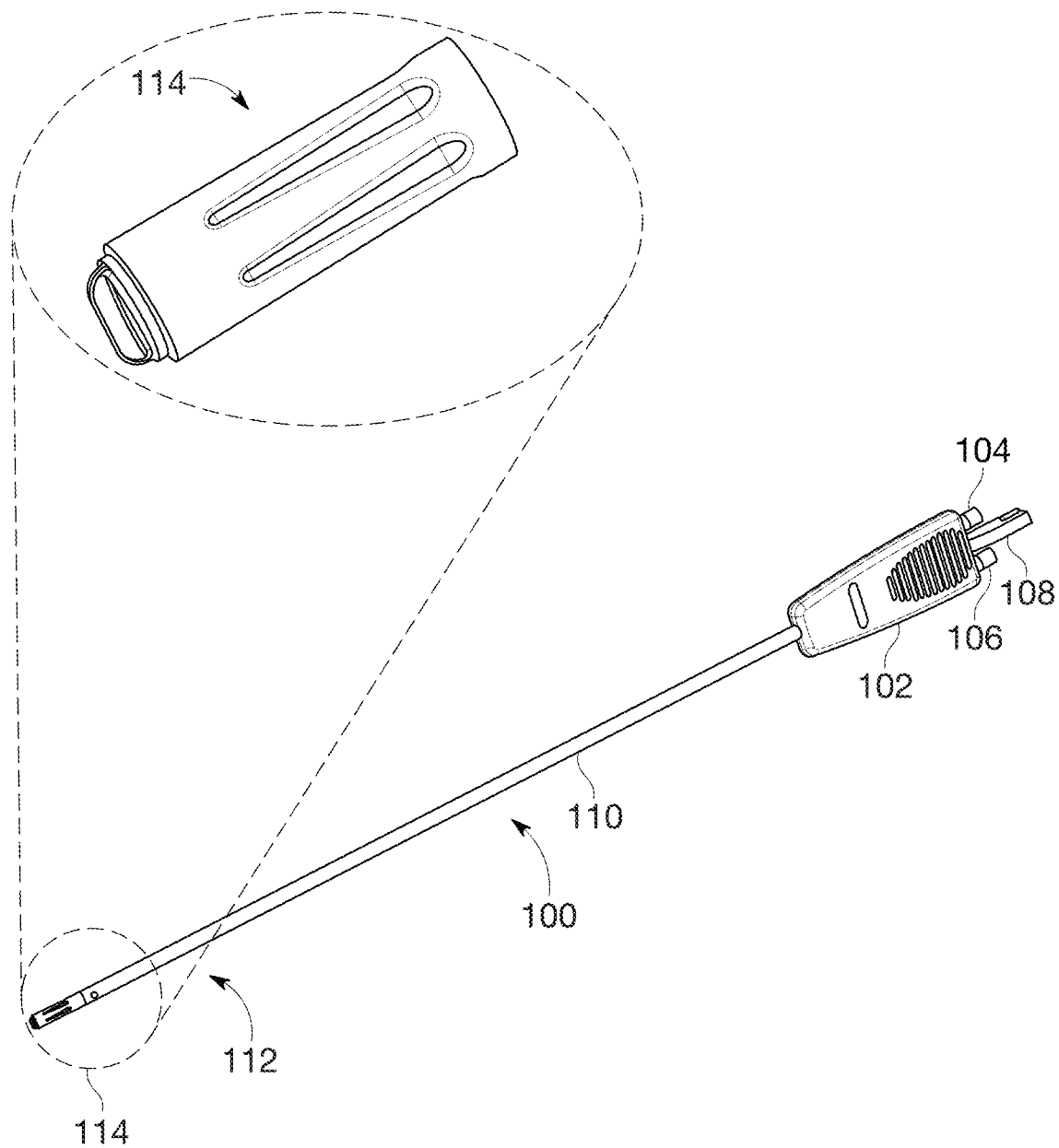
FIG. 1 is a perspective view of a dispensing device having an anti-clogging spray tip that is used for spraying two fluids that react together, in accordance with one embodiment of the present patent application.

Referring to FIG. 1, in one embodiment, a dispensing device 100 for spraying fluids may include one or more of the features disclosed in one or more embodiments of US 2018/0177978 to Spivey et al., assigned to Ethicon LLC, the disclosure of which is hereby incorporated by reference herein. In one embodiment, the dispensing device 100 preferably includes a device housing 102 that contains a manifold (not shown) and two Luer-type connections 104, 106 that extend proximally from the device housing. In one embodiment, the two Luer-type connectors 104, 106 may be connected to two syringes that contain respective fluids that react with one another. The dispensing device 100 desirably includes a brace 108 that is configured to connect the device housing 102 with a structure containing the two syringes. A first syringe may contain a first fluid and a second syringe may include a second fluid that reacts with the first fluid upon being sprayed from the dispensing device 100.

Figure 2:
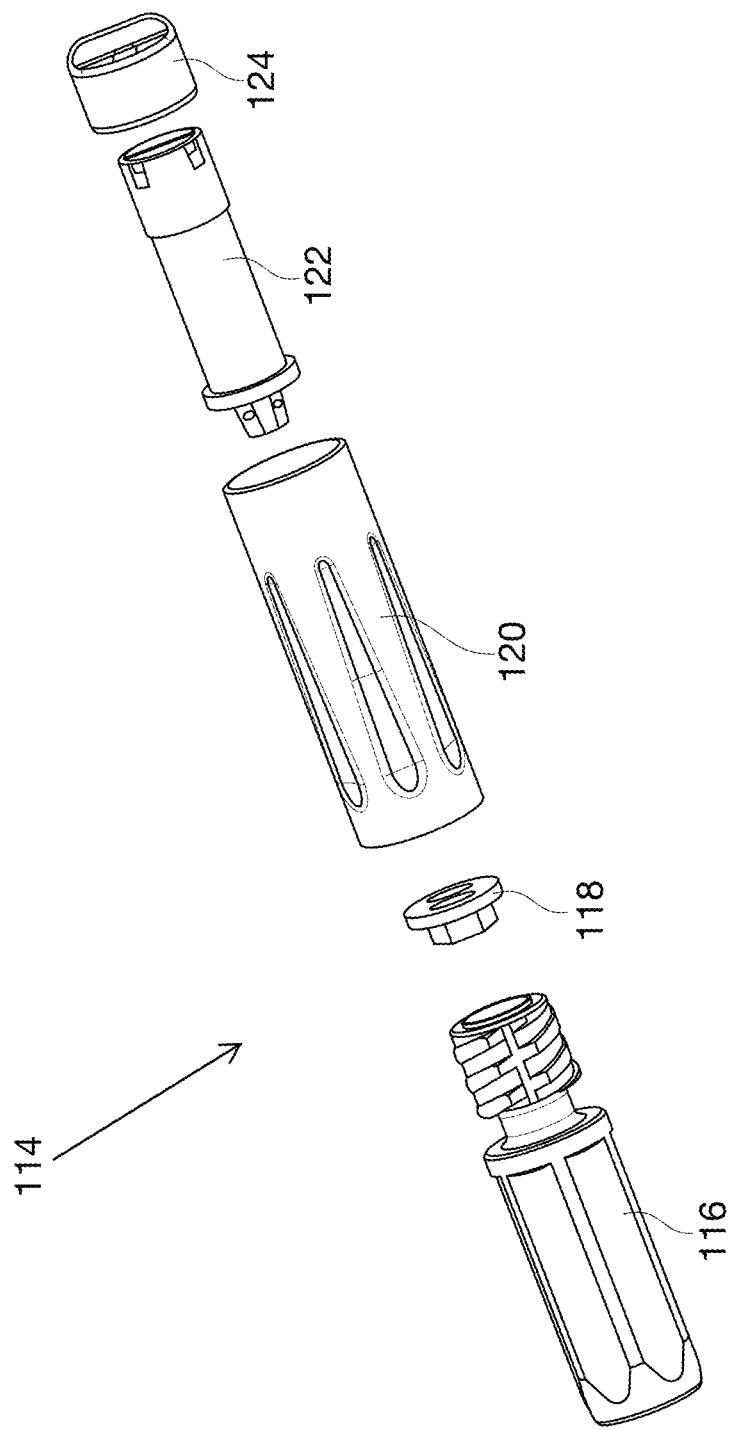
FIG. 2 is an exploded view of an anti-clogging spray tip used for spraying two fluids that react together including a gasket, a tip housing, an inner manifold, and a dispensing cap, and a connector used to secure the anti-clogging spray tip to the distal end of a shaft of a dispensing device, in accordance with one embodiment of the present patent application.

In one embodiment, the dispensing device 100 preferably includes an elongated shaft 110 (e.g., an elongated flexible or rigid tube) having a proximal end that is connected to the device housing 102. The elongated shaft 110 preferably extends distally from the device housing. In one embodiment, the elongated shaft 110 contains two cannulas, which are desirably side-by-side and used to deliver two fluids to a connector 116 secured to a distal end 112 of the elongated shaft 110. A first fluid may be delivered through the first cannula and a second fluid may be delivered through the second cannula. In one embodiment, the dispensing device 100 preferably includes an anti-clogging spray tip 114 that is secured to the distal end 112 of the elongated shaft 110 via a connector 116 (FIG. 2). Upon being sprayed from the anti-clogging spray tip 114, the two fluids preferably react with one another.

In one embodiment, the anti-clogging spray tip 114 may be permanently secured to the distal end 112 of the elongated shaft 110. In one embodiment, the anti-clogging spray tip 114 may be releasably secured to the distal end 112 of the elongated shaft 110 so that a first spray tip (e.g., a used spray tip) may be detached and replaced by a second spray tip (e.g., a new spray tip) that may be releasably secured to the distal end of the shaft.

Referring to FIG. 2, in one embodiment, the anti-clogging spray tip 114 (FIG. 1) preferably includes various components that are assembled together for use in spraying two fluids from the distal end of the dispensing device 100 (FIG. 1). In one embodiment, the anti-clogging spray tip 114 preferably includes a gasket 118, a tip housing 120, an inner manifold 122, and a dispensing cap 124. In one embodiment, the above-listed components of the anti-clogging spray tip 114 (FIG. 1) are assembled together and the fully assembled anti-clogging spray tip 114 is secured to the distal end 112 of the tubular shaft 110 of the dispensing device 100 (FIG. 1) via the connector 116. In one embodiment, the connector 116 is not part of the anti-clogging spray tip 114, but is used for connecting the spray tip to a distal end of a shaft of a dispensing device. In one embodiment, an anti-clogging spray tip may include a connector that is used for securing the spray tip to the distal end of a shaft of a dispensing device.

Figure 3A:
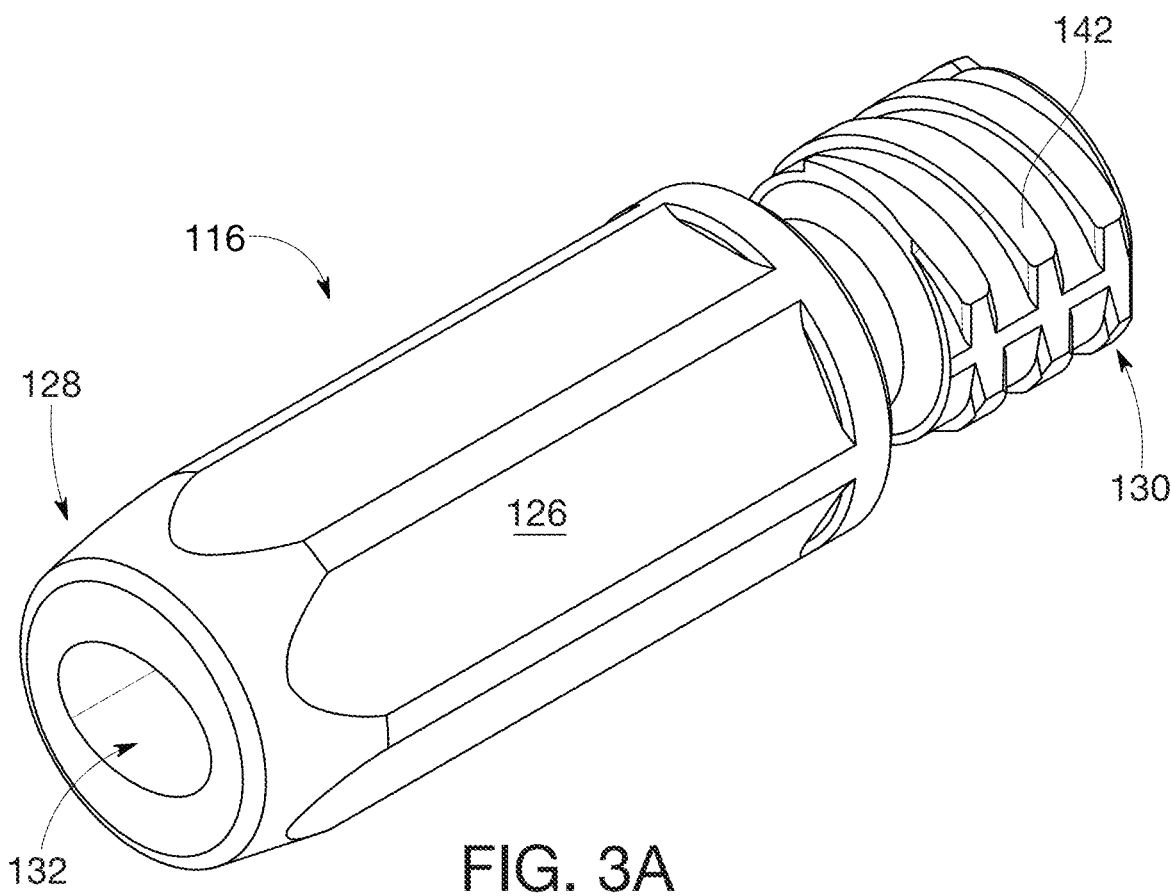
FIG. 3A is a perspective view of the connector shown in FIG. 2.
Figure 3B:
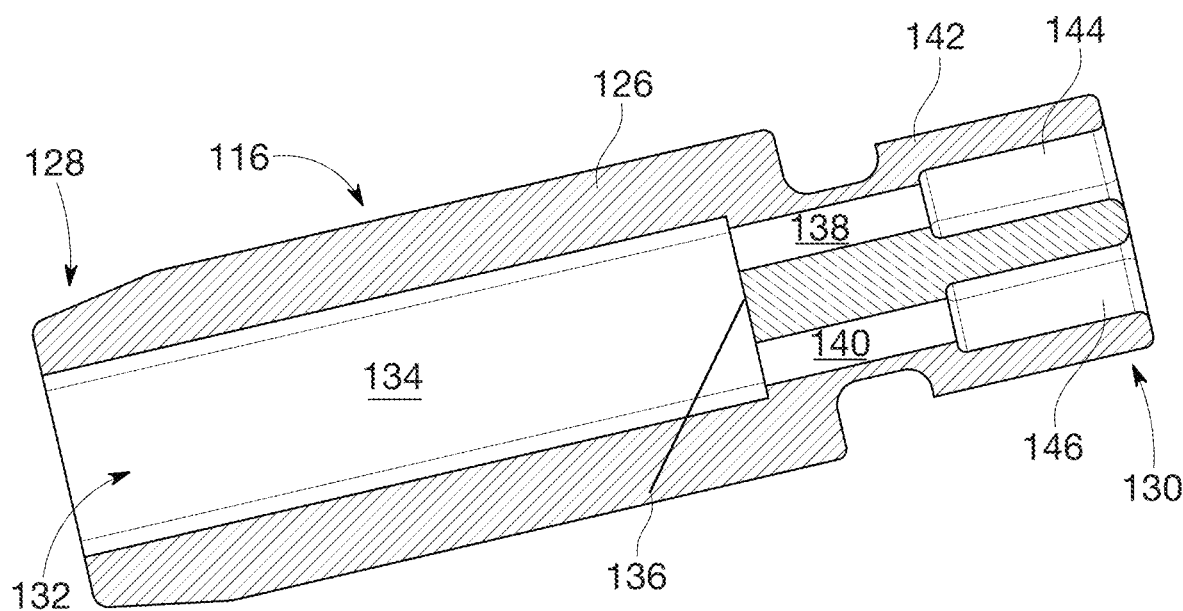
FIG. 3B is a cross-sectional view of the connector shown in FIG. 3A.

Referring to FIGS. 3A and 3B, in one embodiment, the connector 116 preferably includes a tube-shaped body 126 that is secured to the distal end 112 of the elongated shaft 110 of the dispensing device (FIG. 1). In one embodiment, the connector 166 preferably includes a proximal end 128, a distal end 130, an inlet opening 132 at the proximal end 128 that is adapted to receive the distal end 112 of the elongated shaft 110 of the dispensing device 100 (FIG. 1), and a connector flow chamber 134 that extends between the inlet opening 132 and an end wall 136 that defines an end of the connector flow chamber 134.

In one embodiment, the connector 116 preferably includes a first lumen 138 that extends between the connector flow chamber 134 and the distal end 130 of the connector. The first lumen 138 is adapted to receive a first cannula for a first fluid. The connector 116 preferably includes a second lumen 140 that extends between the connector flow chamber 134 and the distal end 130 of the connector. The second lumen 140 is adapted to receive a second cannula for a second fluid that reacts with the first fluid. In one embodiment, the first and second fluids are preferably separated from one another as they pass through the connector 116. The first and second lumens 138, 140 are preferably side-by-side and are adapted to receive and seat respective first and second cannulas that extend through the tubular shaft 110 of the dispensing device 100 (FIG. 1).

In one embodiment, the distal end 130 of the connector 116 preferably has external threads 142 that are adapted to be threaded into internal threads provided inside the tip housing 120 (FIG. 2) for assembling the proximal end of the tip housing with the connector 116, as will be described in more detail herein.

Figure 3C:
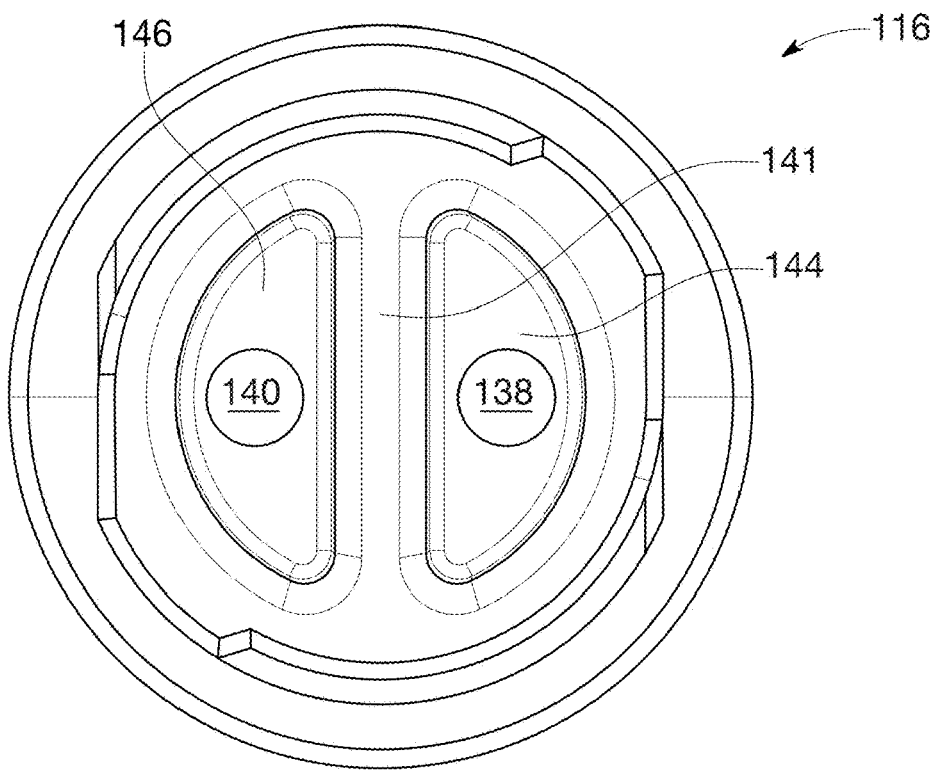
FIG. 3C is a distal end view of the connector shown in FIG. 3A.

Referring to FIGS. 3B and 3C, in one embodiment, the distal end 130 of the connector 116 preferably includes a first D-shaped exit port 144 that is aligned with a distal end of the first lumen 138, and a second D-shaped exit port 146 that is aligned with the distal end of the second lumen 140. The connector 116 desirably includes a connector dividing wall 141 that divides and spaces the first and second D-shaped exit ports 138, 140 from one another. As will be described in more detail herein, the first and second D-shaped exit ports 144, 146 are adapted to receive first and second D-shaped attachment plugs projecting from a proximal face of the gasket 118 (FIG. 2) for assembling the gasket 118 with the distal end 130 of the connector 116. In one embodiment, the two fluids are preferably maintained separate and apart from one another until they are sprayed from the dispensing cap 124 (FIG. 2) located at the distal end of the anti-clogging spray tip 114 (FIG. 1), whereupon the two fluids are mixed together for reacting with one another.

Figure 3D:
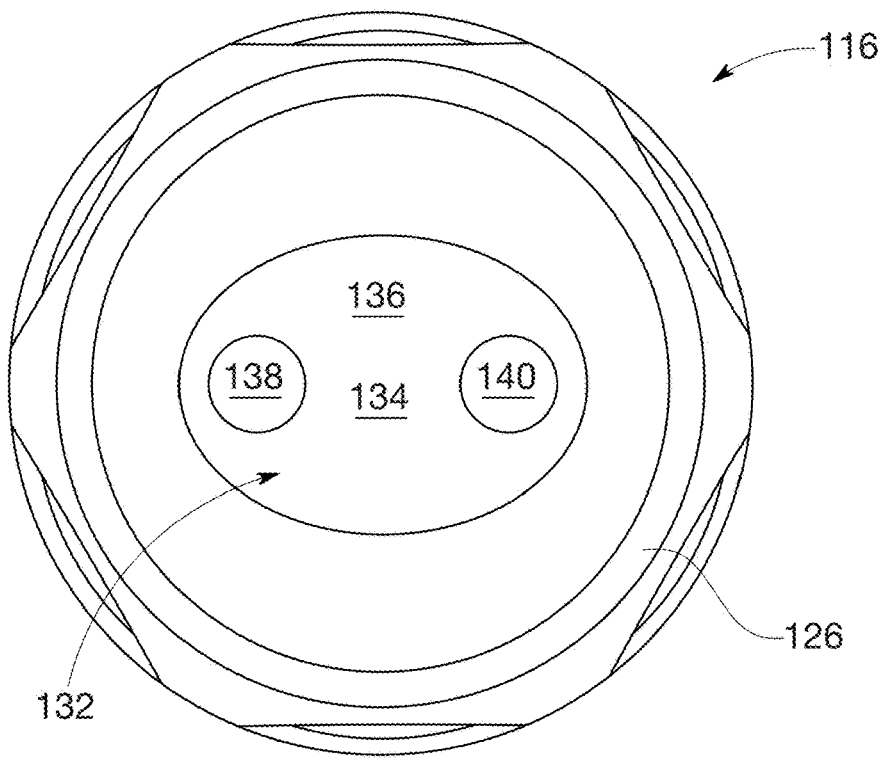
FIG. 3D is a proximal end view of the connector shown in FIG. 3A.

Referring to FIG. 3D, in one embodiment, the inlet opening 132 of the connector 116 provides access to the proximal end 128 (FIG. 3A) of the connector flow chamber 134, which is located at the proximal end of the tubular member 126 of the connector 116. The connector flow chamber 134 desirably terminates at the distal end wall 136. The first and second lumens 138, 140 are preferably formed in the distal end wall 136 and extend distally toward the respective D-shaped exits ports 144, 146 located at the distal end 130 of the connector 116. The first lumen 138 is adapted to receive a first cannula that contains a first fluid of a multiple component material and the second lumen 140 is adapted to receive a second cannula that contains a second fluid of the multiple component material.

Referring to FIGS. 4A-4D, in one embodiment, the gasket 118 preferably includes an annular plate 148 having a proximal face 150 that faces toward a proximal end of the anti-clogging spray tip 114 (FIG. 2) and a distal face 152 that extends toward the distal end of the anti-clogging spray tip. The gasket 118 desirably includes a first D-shaped attachment plug 154 that is configured to be inserted into the first D-shaped exit port 144 at the distal end 130 of the connector 116 (FIG. 3B). The gasket 118 desirably includes a second D-shaped attachment plug 156 that is adapted to be inserted into the second D-shaped exit port 146 located at the distal end 130 of the connector 116 (FIG. 3B). The first and second D-shaped attachment plugs 154, 156 preferably have an outer dimension and configuration that closely matches the shape of the respective D-shaped exit ports 144, 146 located at the distal end 130 of the connector 116 for forming a press fit between the gasket 118 and the distal end of the connector 116.

In one embodiment, the gasket 118 preferably includes a first lumen 138' that extends through the first D-shaped plug 154 to the distal end face 152 of the annular plate 148. The gasket 118 desirably includes a second lumen 140' that extends through the second D-shaped plug 156 to the distal end face 152 of the annular plate 148.

In one embodiment, when the gasket 118 is assembled with the distal end 130 of the connector 116 (FIG. 3B), the first D-shaped attachment plug 154 is preferably inserted into the first D-shaped exit port 144 of the connector and the second D-shaped attachment plug 156 is inserted into the second D-shaped exit port 146 of the connector. After the gasket 118 has been assembled with the distal end of the connector 116, the first lumen 138 extending through the connector is preferably in alignment with the first lumen 138' of the gasket 118 and the second lumen 140 extending through the connector 116 is preferably in alignment with the second lumen 140' of the gasket 118.

Figure 4A:
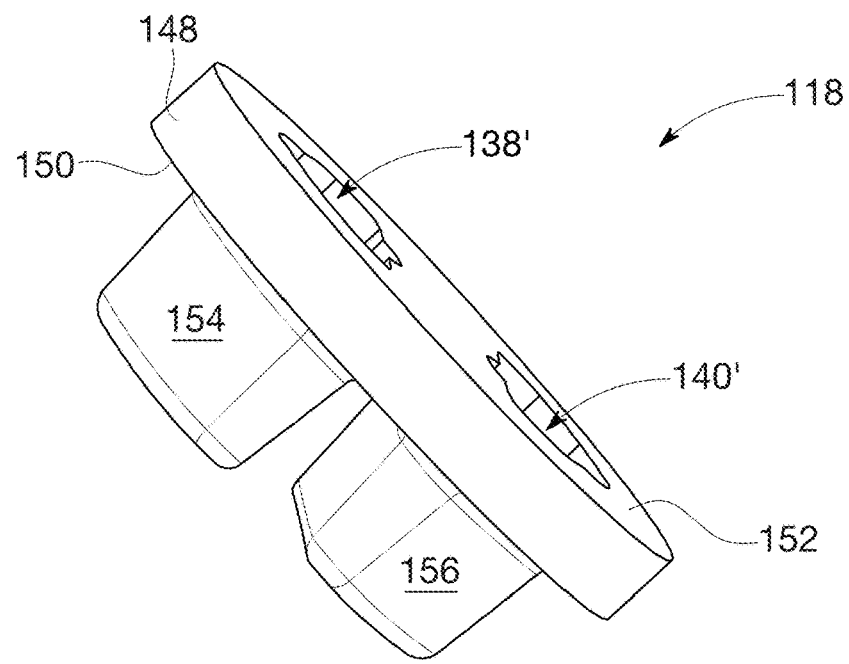
FIG. 4A is a perspective view of the gasket shown in FIG. 2.
Figure 4B:
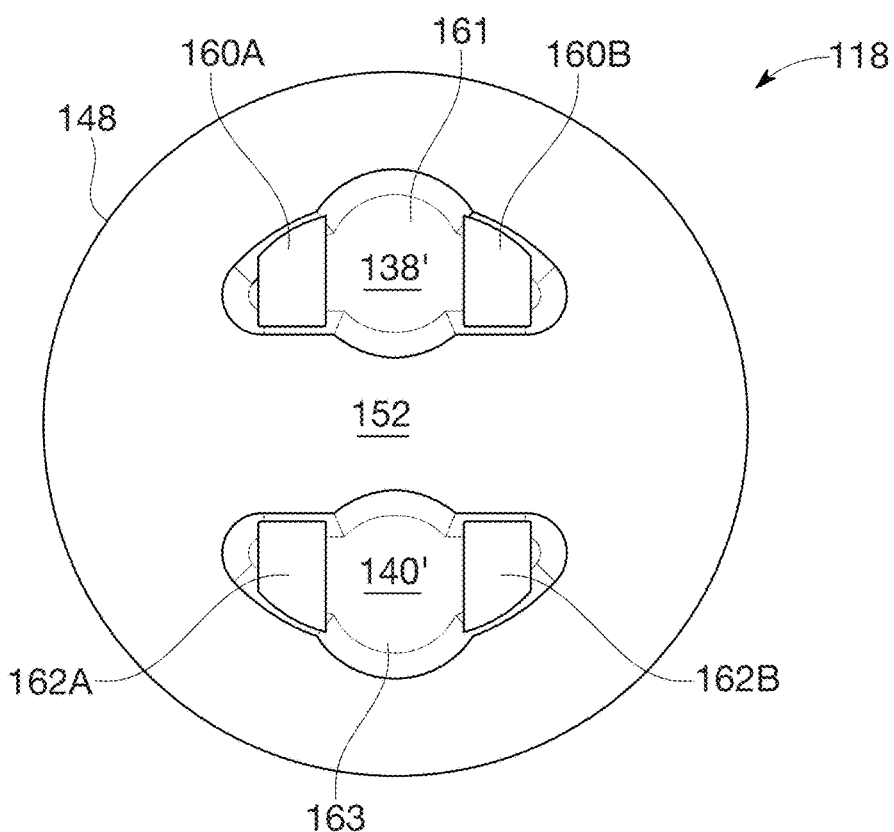
FIG. 4B is a distal end view of the gasket shown in FIG. 4A.
Figure 4C:
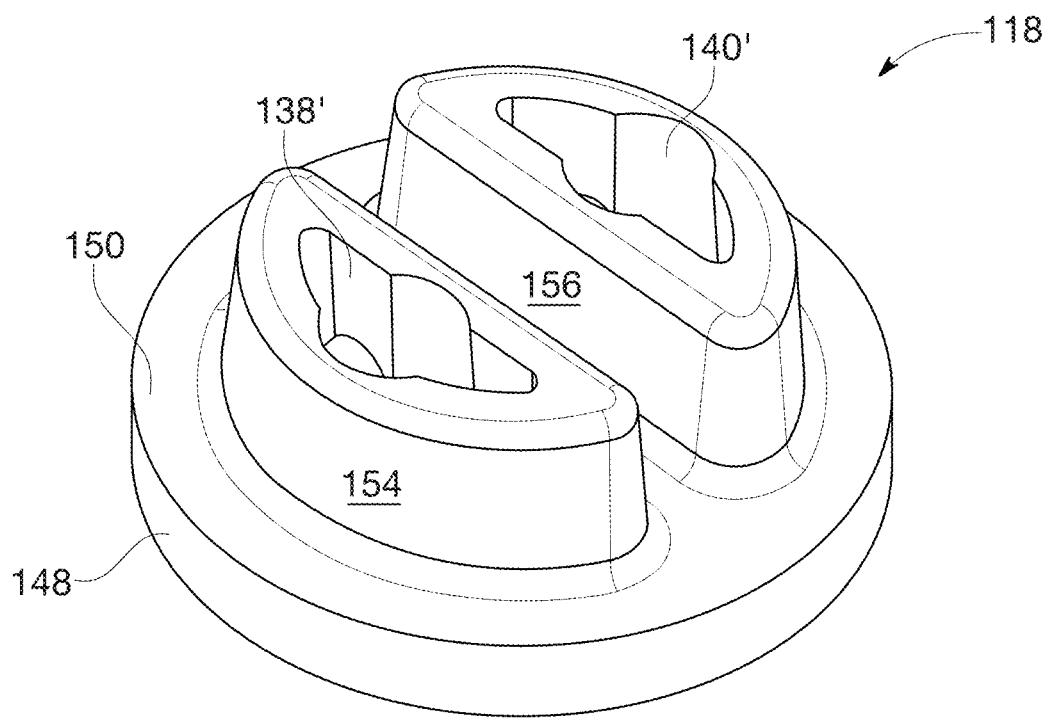
FIG. 4C is a perspective view of a proximal side of the gasket shown in FIG. 4A.
Figure 4D:
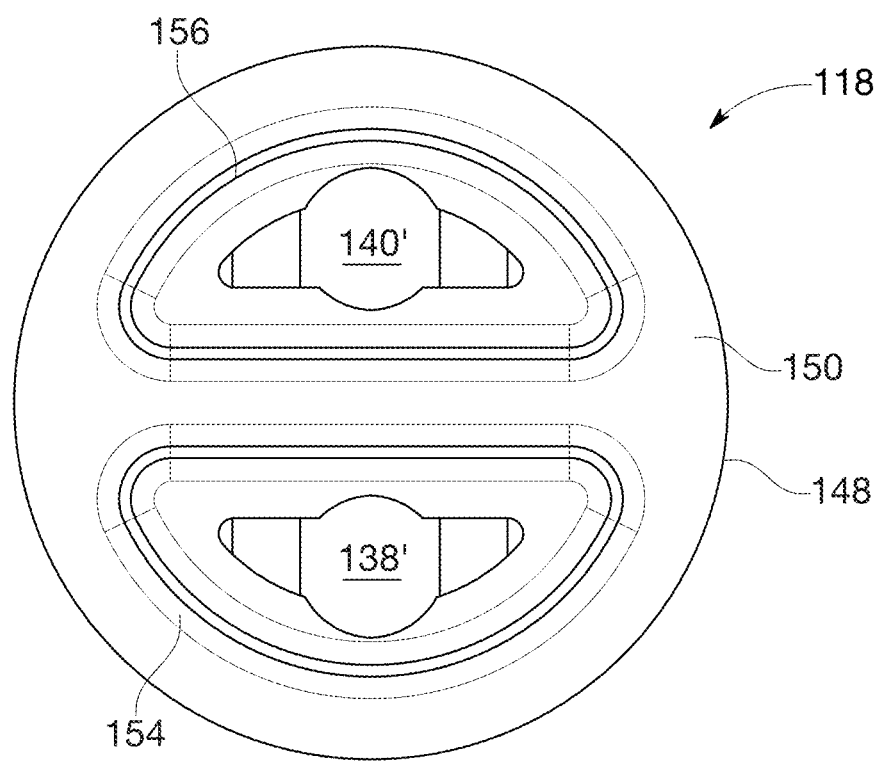
FIG. 4D is a proximal end view of the gasket shown in FIG. 4A.
Figure 6A:
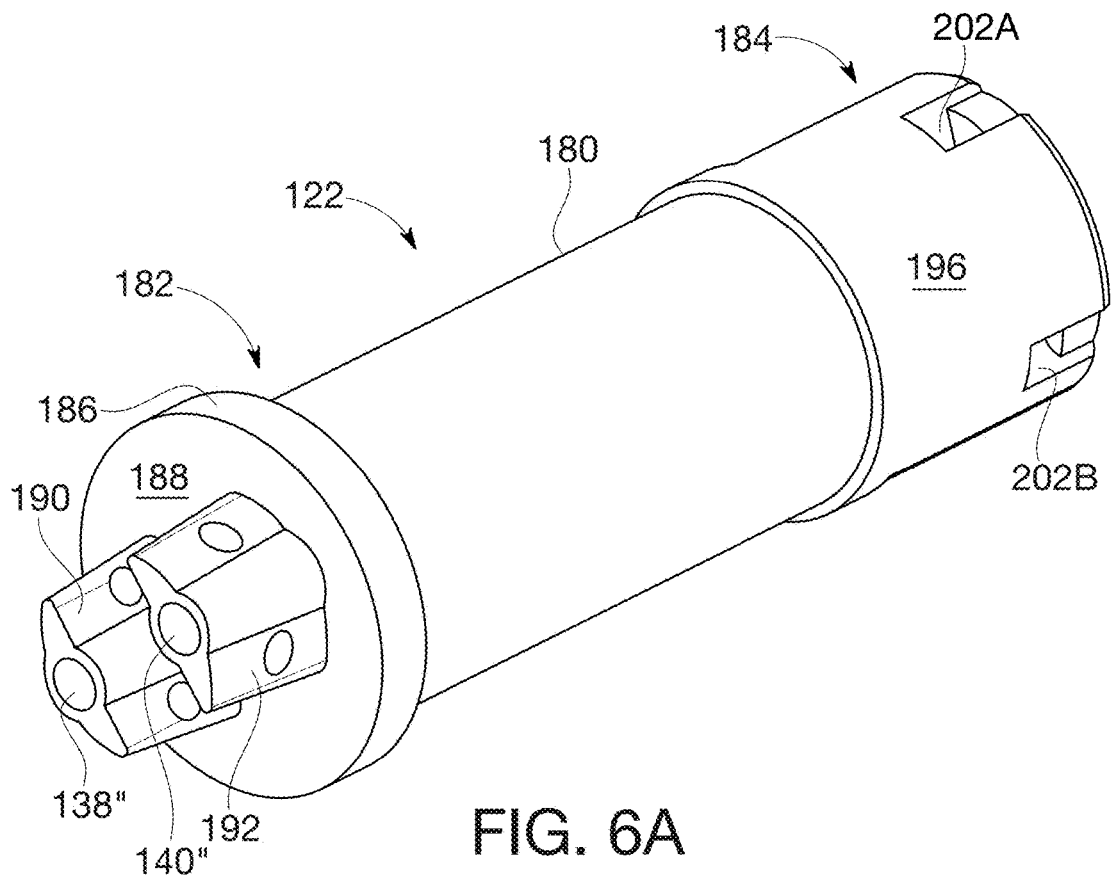
FIG. 6A is a perspective view of the inner manifold shown in FIG. 2.

Referring to FIG. 4B, in one embodiment, the gasket 118 desirably includes a first pair of lateral struts 160A, 160B that extend across the first lumen 138'. The lateral struts 160A, 160B are preferably positioned between the proximal end of the D-shaped attachment plug 154 and the distal face 152 of the annular plate 148. The gasket 118 desirably includes a second pair of laterally extending struts 162A, 162B that extend across the second lumen 140' of the gasket 118. The second pair of laterally extending struts 162A, 162B is preferably positioned between the proximal end of the second D-shaped attachment plug 156 and the distal face 152 of the annular plug 148. As will be described in more detail herein, the laterally extending struts 160A-160B and 162A-162B preferably seat the free ends of butterfly-shaped connectors that extend proximally from a proximal end of the inner manifold 122 (FIG. 6A).

In one embodiment, the distal face 152 of the annular plate 148 of the gasket 118 includes a first butterfly-shaped opening 161 that is aligned with the first lumen 138'. The first butterfly-shaped opening 161 is configured to receive a first butterfly-shaped connector that extends proximally from the inner manifold 122 (FIG. 2). In one embodiment, the distal face 152 of the annular plate 148 of the gasket 118 includes a second butterfly-shaped opening 163 that is aligned with the second lumen 140'. The second butterfly-shaped opening 163 is configured to receive a second butterfly-shaped connector that extends proximally from the inner manifold 122 (FIG. 2).

Figure 5A:
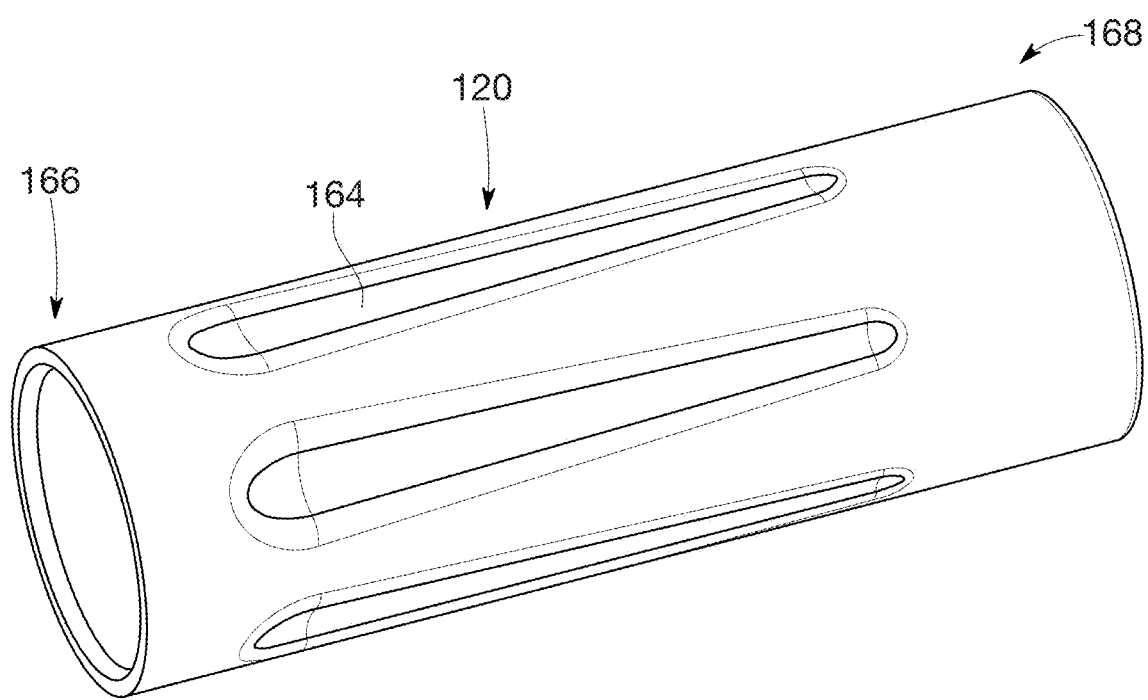
FIG. 5A is a perspective view of the housing shown in FIG. 2.
Figure 5B:
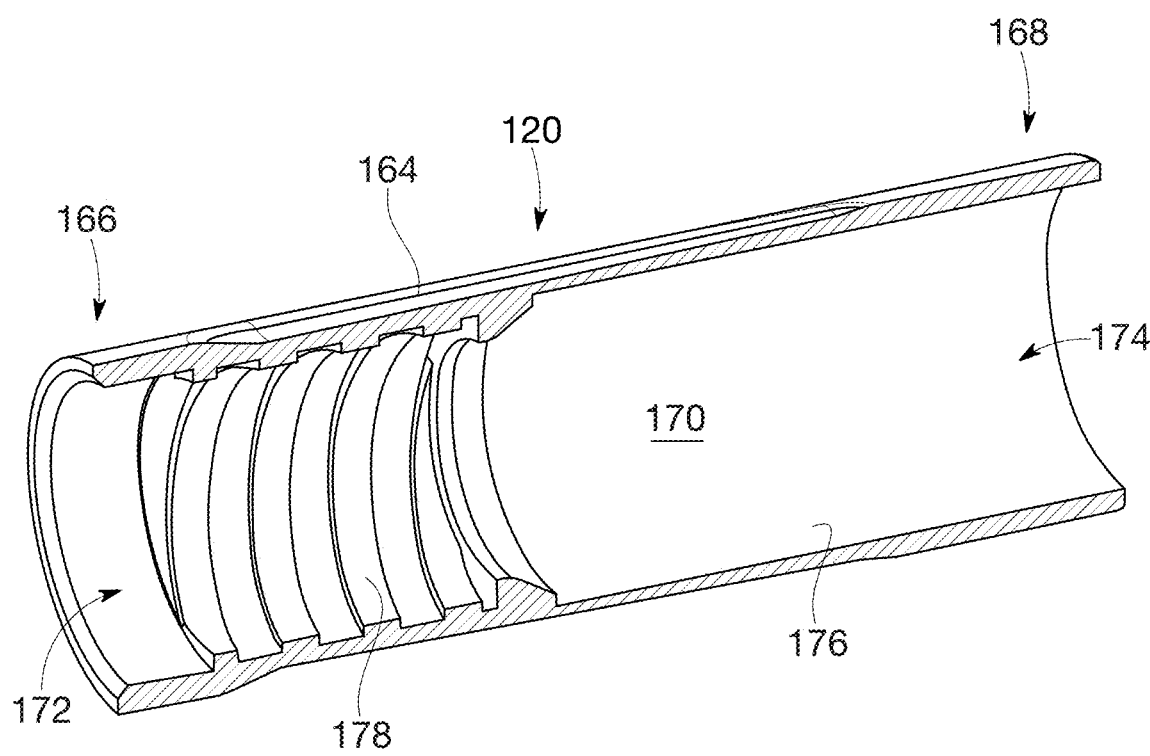
FIG. 5B is a cross-sectional view of the housing shown in FIG. 5A.

Referring to FIGS. 5A and 5B, in one embodiment, the tip housing 120 (FIG. 2) of the anti-clogging spray tip preferably includes a tubular-shaped body 164 having a proximal end 166 and a distal end 168. The tubular-shaped body 164 of the tip housing 120 desirably includes an elongated conduit 170 that extends from a first opening 172 located at the proximal end 166 of the tubular member 164 and a second opening 174 located at the distal end 168 of the tubular member 164.

Referring to FIG. 5B, in one embodiment, the tubular member 164 has an inner surface 176 that surrounds the elongated conduit 170 and that extends from the proximal end 166 to the distal end 168 of the tubular member 164. In one embodiment, the tip housing 120 preferably has internal threads 178 that are formed in the inner surface 176 of the tubular member 164. In one embodiment, the internal threads 178 are preferably adjacent the proximal end 166 of the tubular member 164. The internal threads 168 are adapted to receive the external threads 142 at the distal end of the connector 116 (FIG. 3A) for securing the distal end of the connector 116 with the proximal end of the tip housing 120, with the gasket 118 (FIG. 2) being positioned between the distal end of the connector 116 and the tip housing 120.

Referring to FIG. 6A-6D, in one embodiment, the inner manifold 122 (FIG. 2) preferably includes a tubular member 180 having a proximal end 182 and a distal end 184. The inner manifold 122 desirably includes an annular sealing flange 186 that is secured to the proximal end 182 of the tubular member 180. In one embodiment, the annular sealing flange 186 desirably includes a proximal face 188 that is adapted to abut against the distal face 152 of the gasket 118 (FIG. 4A) when the components of the anti-clogging spray tip are assembled together. In one embodiment, the inner manifold 122 desirably includes a first butterfly-shaped connector 190 that projects proximally from the proximal face 188 of the annular sealing flange 186. The inner manifold 122 desirably includes a second butterfly-shaped connector 192 that also projects proximally from the proximal face 188 of the annular sealing flange 186 of the inner manifold 122. In one embodiment, the first and second butterfly-shaped connectors 190, 192 are adapted to be inserted into the respective butterfly-shaped openings 161, 163 formed in the distal face 152 of the annular plate 148 of the gasket 118 (FIG. 4B).

Figure 6B:
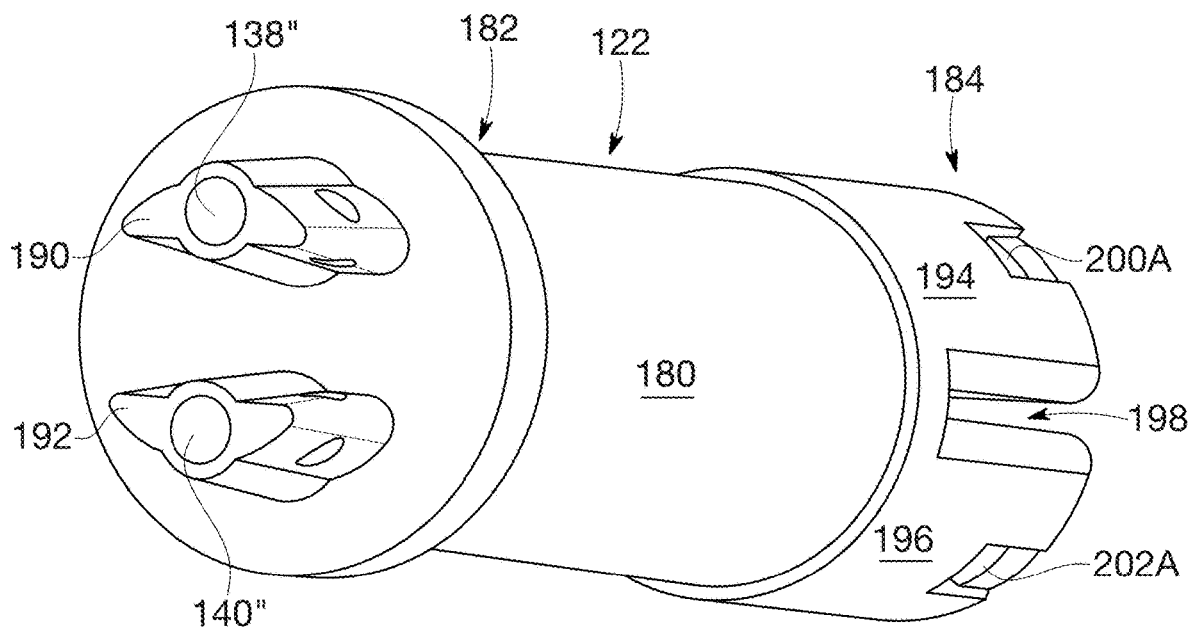
FIG. 6B is another perspective view of the inner manifold shown in FIG. 6A.
Figure 6C:
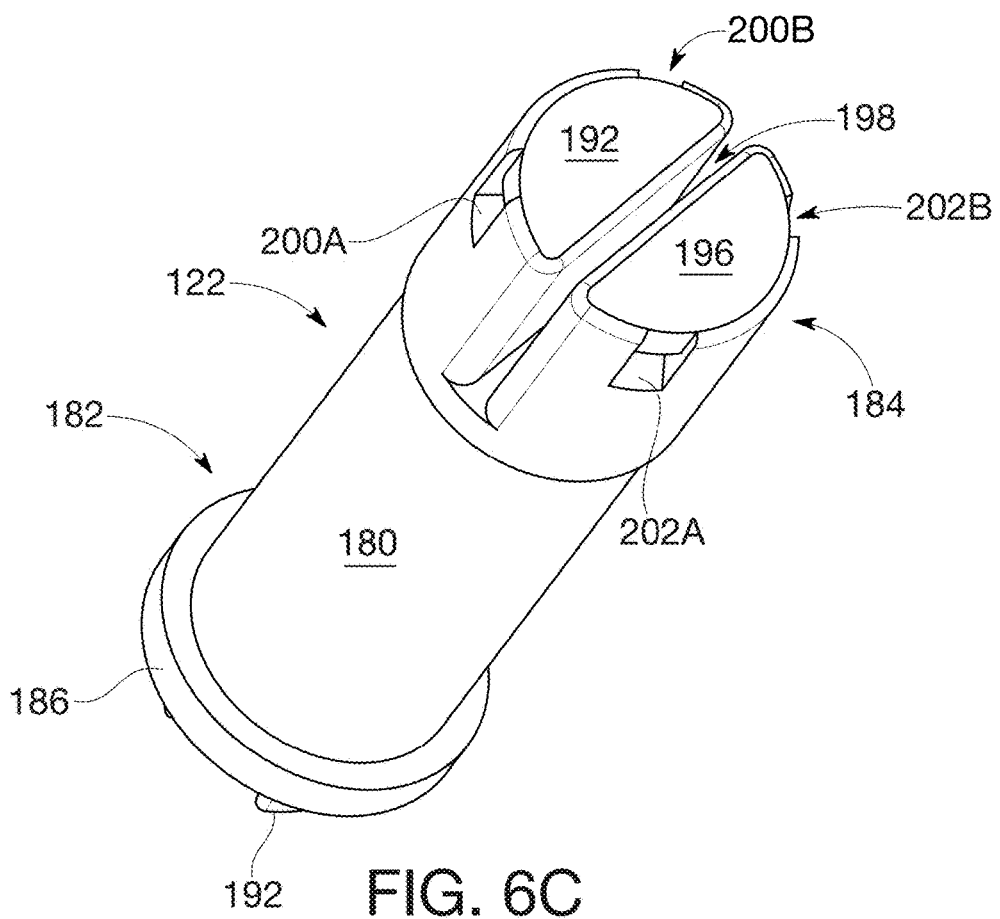
FIG. 6C is a perspective view of a distal end of the inner manifold shown in FIGS. 6A and 6B.

In one embodiment, the first butterfly-shaped connector 190 desirably includes a first lumen 138" that is adapted to be aligned with the first lumen 138' (FIG. 4B) of the gasket 118 and the first lumen 138 of the connector 116 (FIG. 3B). In one embodiment, the second butterfly-shaped connector 192 desirably includes a second lumen 140" that is adapted to be aligned with the second lumen 140' of the gasket 118 (FIG. 4B) and the second lumen 140 of the connector (FIG. 3B). When the connector, the gasket, the tip housing and the inner manifold are assembled together, a first cannula for a first fluid preferably passes through the first lumen 138 of the connector 116 (FIG. 3B), the first lumen 138' of the gasket 118 (FIG. 4B), and the first lumen 138" of the first butterfly-shaped connector 190 (FIG. 6B), and a second cannula for a second fluid preferably passes through the second lumen 140 of the connector 116 (FIG. 3B), the second lumen 140' of the gasket 118 (FIG. 4B), and the second lumen 140" of the second butterfly-shaped connector 192 (FIG. 6B).

In one embodiment, the distal end 184 of the tubular member 180 of the inner manifold 122 is bifurcated into a first terminal chamber 194 for a first fluid of a multiple component material and a second terminal chamber 196 for a second fluid of the multiple component material. The distal end 184 of the tubular member 180 preferably includes a space 198 that extends between the first and second terminal chambers 194, 196 for spacing the first and second terminal chambers from one another. In one embodiment, the first fluid of a multiple component material is passed through the first lumen 138" for being directed into the first terminal chamber 194, and the second fluid of the multiple component material is passed through the second lumen 140" for being directed into the second terminal chamber 196. In one embodiment, the first and second terminal chambers 194, 196 maintain the first and second fluids away from one another.

In one embodiment, the first terminal chamber 194 desirably has an outer wall with radial openings 200A, 200B formed therein that enable the first fluid of the multiple component material to exit radially from the first terminal chamber. In one embodiment, the second terminal chamber 196 desirably has an outer wall with radial openings 202A, 202B formed therein that enable the second fluid of the multiple component material to exit radially the second terminal chamber.

Figure 6D:
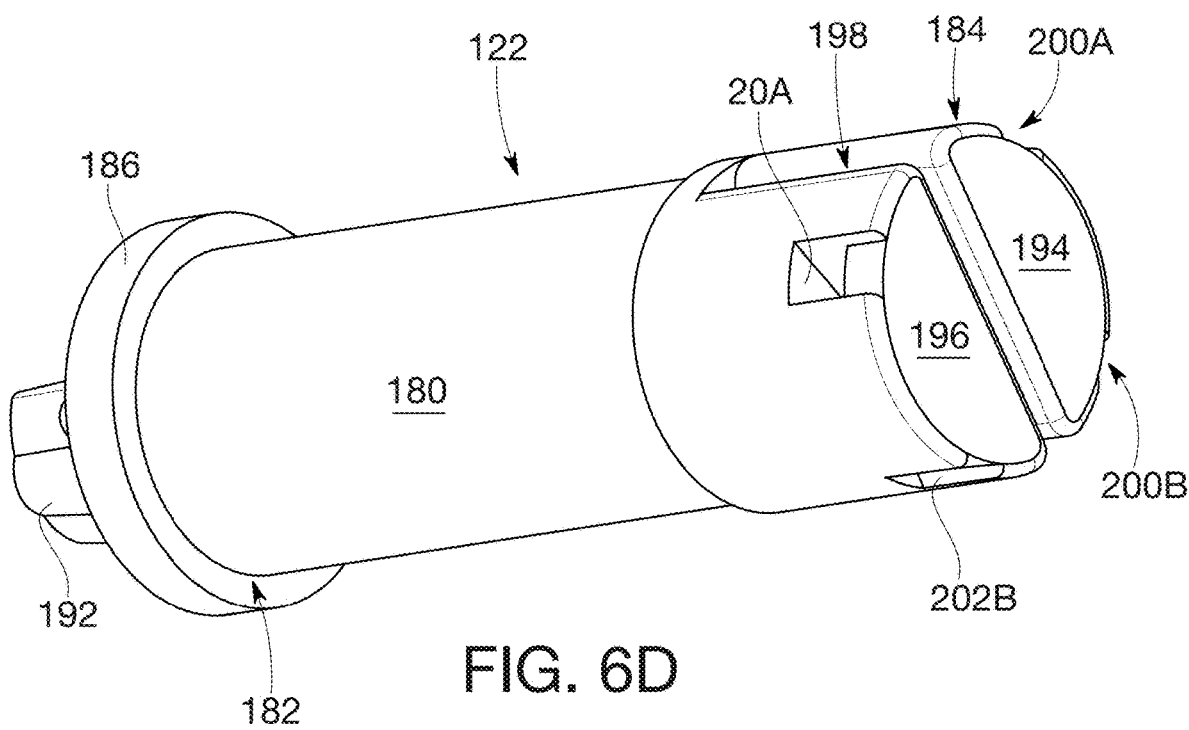
FIG. 6D is another perspective view of the distal end of the inner manifold shown in FIGS. 6A-6C.
Figure 6E:
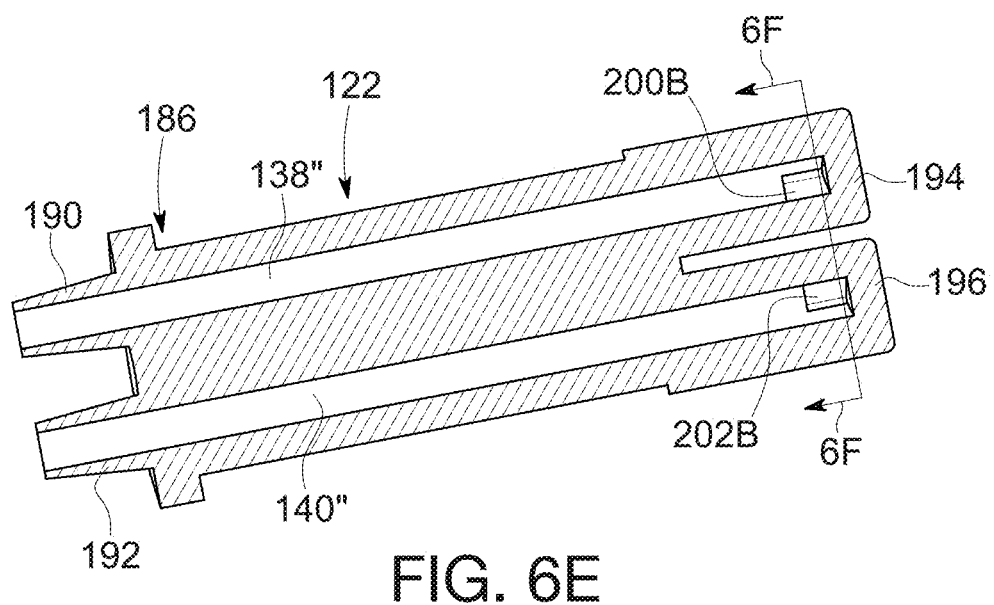
FIG. 6E is a cross-sectional view of the inner manifold shown in FIGS. 6A-6D.

Referring to FIG. 6E, in one embodiment, the inner manifold 122 preferably includes the first lumen 138" that extends through the first butterfly-shaped connector 190 and the annular seal 186 to an end wall at the distal end of the first terminal chamber 194. In one embodiment, the inner manifold 122 preferably includes first radial openings 200A, 200B (FIG. 6C) formed in the outer wall of the first terminal chamber 194 for enabling a first fluid of a multiple component material that flows through the first lumen 138" to exit radially from distal end of the first terminal chamber 194.

The inner manifold 122 preferably includes the second lumen 140" that extends through the second butterfly-shaped connector 192 and the annular seal 186 to an end wall at the distal end of the second terminal chamber 196. In one embodiment, the inner manifold 122 preferably includes second radial openings 202A, 202B (FIG. 6C) formed in the outer wall of the second terminal chamber 196 for enabling a second fluid of the multiple component material that flows through the second lumen 140" to exit radially from the distal end of the second terminal chamber 196.

Figure 6F:
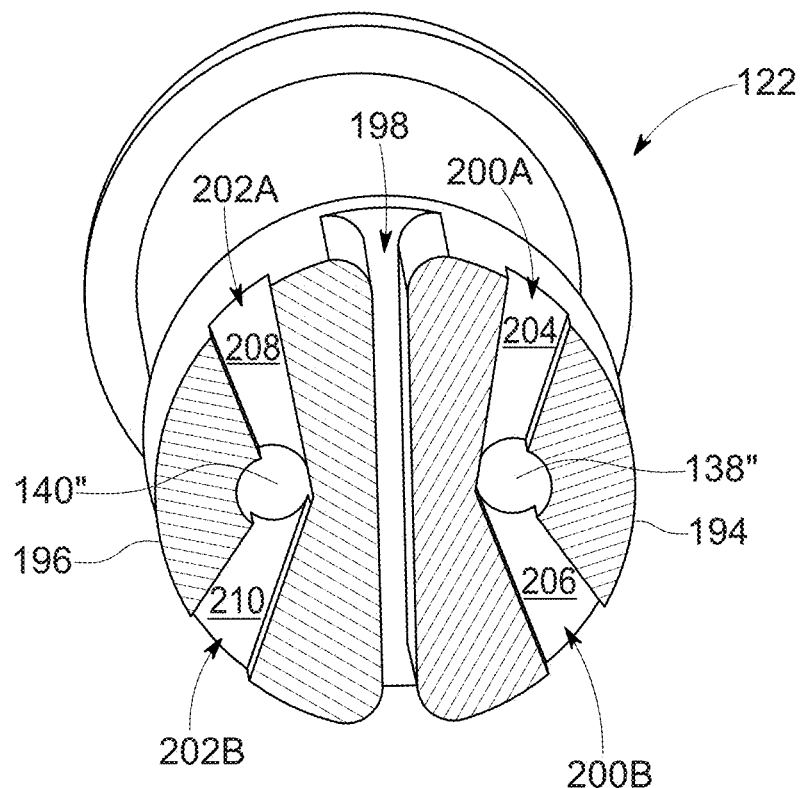
FIG. 6F is a cross-sectional view of the inner manifold shown of FIGS. 6A-6E taken along the line 6F-6F of FIG. 6E.

Referring to FIG. 6F, in one embodiment, the first lumen 138" terminates at an end wall of the first terminal chamber 194. The first terminal chamber 194 preferably includes the first radial openings 200A, 200B that are formed in the outer wall of the first terminal chamber 194. The inner manifold 122 preferably includes first radially-extending flutes 204, 206 that extend outwardly from the first lumen 138" to the respective first radial openings 200A, 200B. In one embodiment, when the first fluid of the multiple component material reaches the distal end of the first lumen 138" it is directed radially outward through the first radially-extending flutes 204, 206 whereupon it exits the distal end of the first terminal chamber 194 via the first radial openings 200A, 200B.

In one embodiment, the second lumen 140" terminates at an end wall of the second terminal chamber 199. The second terminal chamber 196 preferably includes the second radial openings 202A, 202B that are formed in the outer wall of the second terminal chamber 196. The inner manifold 122 preferably includes second radially-extending flutes 208, 210 that extend outwardly from the second lumen 140" to the respective second radial openings 202A, 202B. In one embodiment, when the second fluid of the multiple component material reaches the distal end of the second lumen 140" it is directed radially outward through the second radially-extending flutes 208, 210 whereupon it exits the distal end of the second terminal chamber 196 via the second radial openings 202A, 202B.

In one embodiment, the first and second terminal chambers 194, 196 are spaced from one another via a space 198 that extends therebetween. In one embodiment, opposing walls of the first and second terminal chambers define the space 198. As will be described in more detail herein, the space 198 extending between the first and second terminal chambers 194, 196 may receive a securing flange provided on a proximal side of the dispensing cap 124 (FIG. 2) for securing the dispensing cap to the distal end of the inner manifold 122.

Figure 7A:
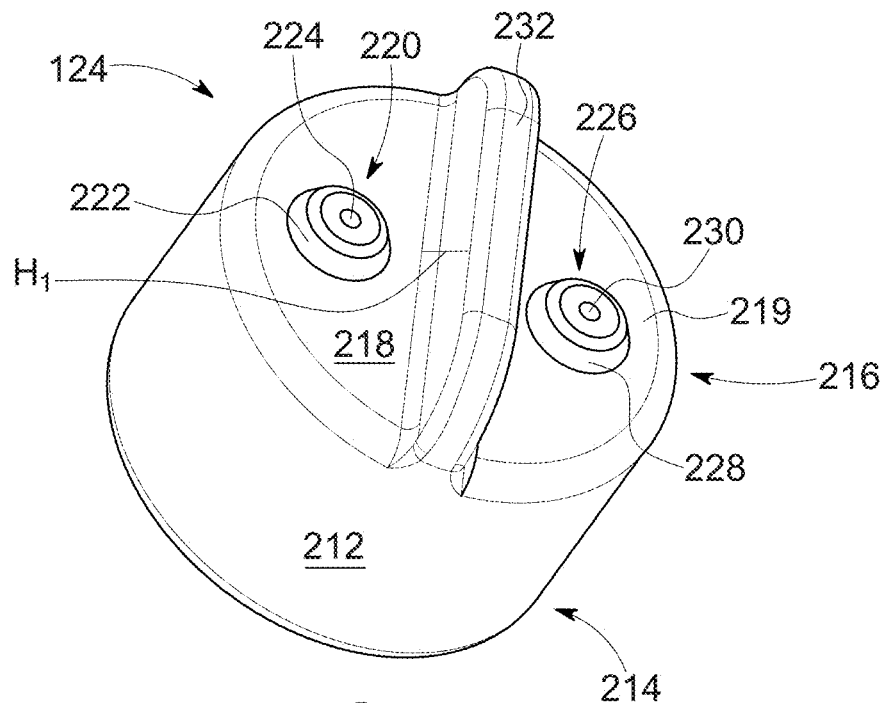
FIG. 7A is a perspective view of a distal end of the dispensing cap shown in FIG. 2.

Referring to FIG. 7A, in one embodiment, the dispensing cap 124 of the anti-clogging spray tip preferably includes a tubular shaped body 212 having a proximal end 214 and distal end 216. The distal end 216 of the dispensing cap 124 preferably has a distal end wall 218 having an outer surface 219. In one embodiment, the dispensing cap 124 preferably includes a first raised orifice 220 having a first raised mound 222 and a first spray opening 224 formed in the first raised mound 222. In one embodiment, the dispensing cap 124 preferably includes a second raised orifice 226 having a second raised mound 228 and a second spray opening 230 formed in the second raised mound 228. In one embodiment, the first and second raised orifices 220, 226 preferably project distally from the outer surface 219 of the distal end wall 218.

In one embodiment, the first fluid of the multiple component material is discharged through the first radial openings 200A, 200B of the first terminal chamber 194 (FIG. 6F), whereupon the first fluid is further directed through the first raised orifice 220 of the dispensing cap 124. In one embodiment, the second fluid of the multiple component material that flows out of the radial openings 202A, 202B of the second terminal chamber 96 (FIG. 6F) is further directed through the second raised orifice 226 of the dispensing cap 124.

In one embodiment, the dispensing cap 124 desirably includes an external dividing wall 232 that projects distally from the outer surface 219 of the distal end wall 218 of the dispensing cap. In one embodiment, the external dividing wall 232 has a height $H_1$ that projects beyond the outer surface 219 of the distal end wall 218 of the dispensing cap 124. In one embodiment, the external dividing wall 232 functions as a barrier between the first and second raised orifices 220, 226 to prevent the first and second fluids that are sprayed from the respective first and second raised orifices from contacting one another and reacting together over the outer surface 219 of the distal end wall 218 of the end cap. Thus, the external dividing wall 232 serves to minimize clogging of one or more of the first and second spray openings 224, 230 of the respective first and second raised orifices 220, 226.

Figure 7B:
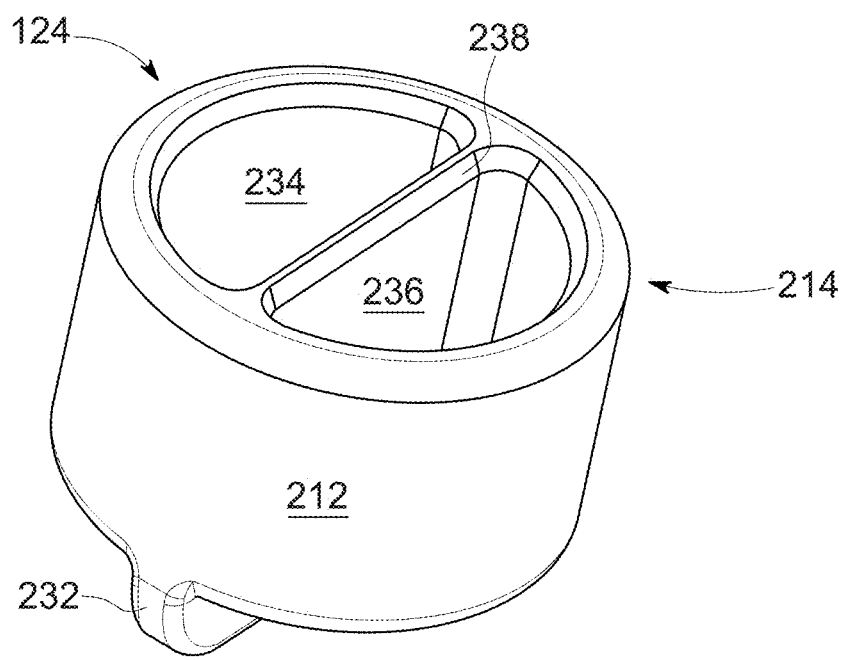
FIG. 7B is a perspective view of a proximal end of the dispensing cap shown in FIG. 7A.

Referring to FIG. 7B, in one embodiment, the proximal end 214 of the tubular body 212 of the dispensing cap 124 preferably includes a first D-shaped chamber 234 that is configured to receive the first terminal chamber 194 located at the distal end 184 of the inner manifold 122 (FIG. 6D). In one embodiment, the dispensing cap 124 desirably includes a second D-shaped chamber 236 that is configured to receive the second terminal chamber 196 located at the distal end 184 of the inner manifold 122. The dispensing cap 124 desirably includes an interior dividing wall 238 that separates the first D-shaped chamber 234 of the inner manifold 122 from the second D-shaped chamber 236 of the inner manifold 122. In one embodiment, when the dispensing cap 124 is assembled with the distal end of the inner manifold 122, the interior dividing wall 238 accessible at the proximal end 214 of the tubular member 212 is preferably inserted into the space 198 extending between the first and second terminal chambers 194, 196 of the inner manifold 122 (FIG. 6B) for securing the dispensing cap 124 to the distal end of the inner manifold 122 (FIG. 2).

Figure 7C:
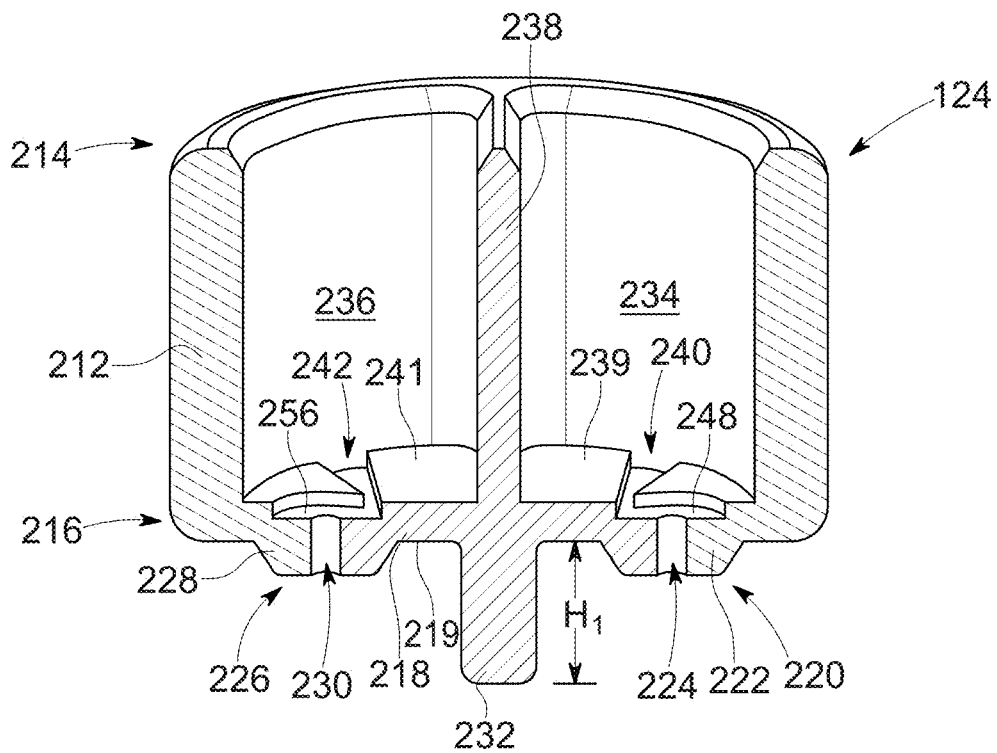
FIG. 7C is a cross-sectional view of the dispensing cap shown in FIGS. 7A and 7B.

Referring to FIG. 7C, in one embodiment, the dispensing cap 124 preferably includes the tubular body 212 having a proximal end 214 and a distal end 216. The dispensing cap 124 preferably includes the first raised orifice 220 having a first raised mound 222 and a first spray opening 224 formed in the first raised mound 222, which is in fluid communication with the first D-shaped chamber 234 of the dispensing cap. The dispensing cap 124 desirably includes a second raised orifice 226 having a second raised mound 228 with a second spray opening 230 formed in the second raised mound 228, which is in fluid communication with the second D-shaped chamber 236 of the dispensing cap. The interior dividing wall 238 divides the first D-shaped chamber 234 from the second D-shaped chamber 236 for insuring that the first and second fluids of the multiple component material remain separated from one another until they are discharged via the first and second spray openings 224, 230 of the respective first and second raised orifices 220, 226.

The exterior dividing wall 232 of the dispensing cap 124 preferably projects distally from the outer surface 219 of the distal end wall 218 of the dispensing cap 124. The exterior dividing wall 232 divides the first and second raised orifices 220, 226 from one another. The exterior dividing wall 232 preferably defines a height $H_1$ that extends above and/or beyond the outer surface 219 of the distal end wall 218 of the dispensing cap 124.

In one embodiment, the first D-shaped chamber 234 includes a first inner surface 239 of the distal end wall 218 having a first fluid pathway 240 formed therein that is in fluid communication with the first spray opening 224 of the first raised orifice 220. In one embodiment, the first fluid of the multiple component material that is directed into the first D-shaped chamber 234 is advanced into the first fluid pathway 240 for being rapidly rotated within the first swirl chamber 248 prior to being dispensed from the first spray opening 224 of the first raised orifice 220 of the dispensing cap 124.

In one embodiment, the second D-shaped chamber 236 includes a second inner surface 241 of the distal end wall having a second fluid pathway 242 formed therein that is in fluid communication with the second spray opening 230 of the second raised orifice 226. In one embodiment, the second fluid of the multiple component material that is directed into the second D-shaped chamber 236 is advanced into the second fluid pathway 242 for being rapidly rotated within the second swirl chamber 256 prior to being dispensed from the second spray opening 230 of the second raised orifice 226 of the dispensing cap 124.

Figure 8A:
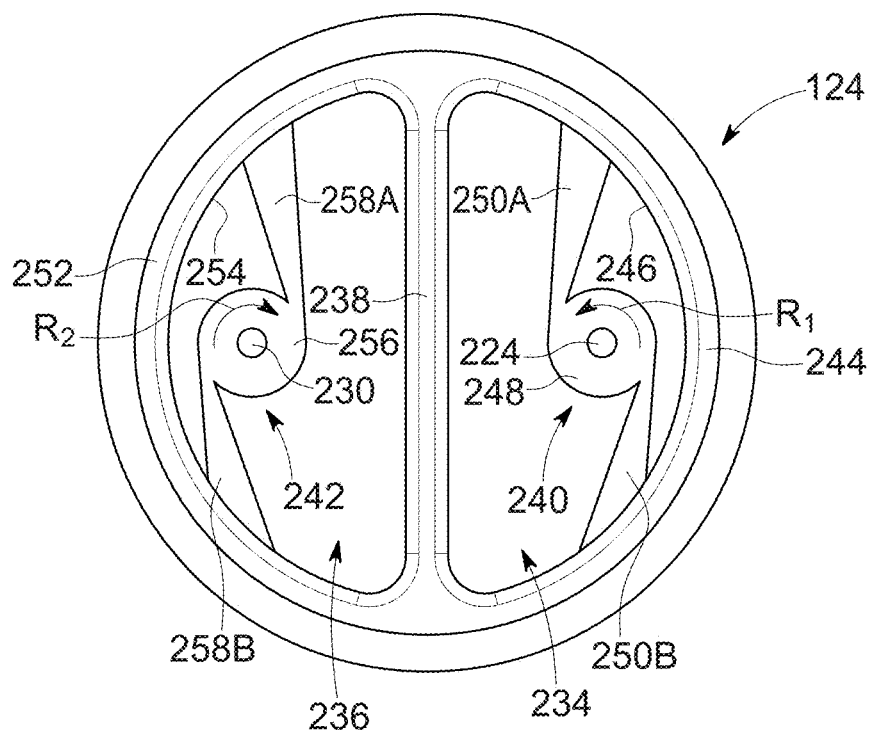
FIG. 8A is a proximal end view of the dispensing cap shown in FIGS. 7A-7C including a first D-shaped chamber having a first fluid pathway and a second D-shaped chamber having a second fluid pathway.

Referring to FIG. 8A, in one embodiment, the dispensing cap 124 preferably includes the interior dividing wall 238 that divides the first D-shaped chamber 234 and the second D-shaped chamber 236 from one another. The first D-shaped chamber 234 preferably includes an outer peripheral wall 244 having an inner surface 246 that is spaced away from the interior dividing wall 238. The first fluid pathway 240 preferably includes the first swirl chamber 248 that surrounds the first spray opening 224 and a pair of first flutes 250A, 250B that extend inwardly from the inner surface 246 of the peripheral wall 244 toward the first swirl chamber 248. In one embodiment, the first flutes 250A, 250B may have respective widths that narrow between the inner surface 246 and the first swirl chamber 248 for increasing the speed of the first fluid as it passes through the first flutes 250A, 250B toward the first swirl chamber 248. In one embodiment, the configuration of the first flutes 250A, 250B relative to the first swirl chamber 248 preferably rotates the first fluid in a counterclockwise direction designated R1 as it enters into the first swirl chamber 248. In one embodiment, the first fluid is rotated in the counterclockwise direction R1 prior to being dispensed/sprayed through the first spray opening 224.

In one embodiment, the second D-shaped chamber 236 preferably includes an outer peripheral wall 252 having an inner surface 254 that is spaced away from the interior dividing wall 238. The second fluid pathway 242 preferably includes the second swirl chamber 256 that surrounds the second spray opening 224 and a pair of second flutes 258A, 258B that extend inwardly from the inner surface 254 of the peripheral wall 252 toward the second swirl chamber 256. In one embodiment, the second flutes 258A, 258B may have widths that narrow between the inner surface 254 of the peripheral wall 252 and the second swirl chamber 256 for increasing the speed of the first fluid as it passes through the second flutes 258A, 258B toward the second swirl chamber 252. The configuration of the second flutes 258A, 258B relative to the second swirl chamber 256 preferably rotates the second fluid in a clockwise direction designated R2 as it enters into the second swirl chamber 252. In one embodiment, the second fluid is rotated in the clockwise direction R2 prior to being dispensed through the second spray opening 230.

In one embodiment, when the first fluid of the multiple component material enters into the first D-shaped chamber 234 of the dispensing cap 124, the first fluid preferably flows into the outer ends of the first flutes 250A, 250B, whereupon the first flutes direct the first fluid into the outer periphery of the first swirl chamber 248 for rotating the first fluid in the counterclockwise direction R1 as it is sprayed from the first spray opening 224. Similarly, when the second fluid of the multiple component material enters into the second D-shaped chamber 236 of the dispensing cap 124, the second fluid preferably flows into the outer ends of the second flutes 258A, 258B, whereupon the second flutes direct the second fluid into the outer perimeter of the second swirl chamber 256 for rotating the second fluid in the clockwise direction R2 as it is sprayed from the second spray opening 230.

Figures 1, 8B:
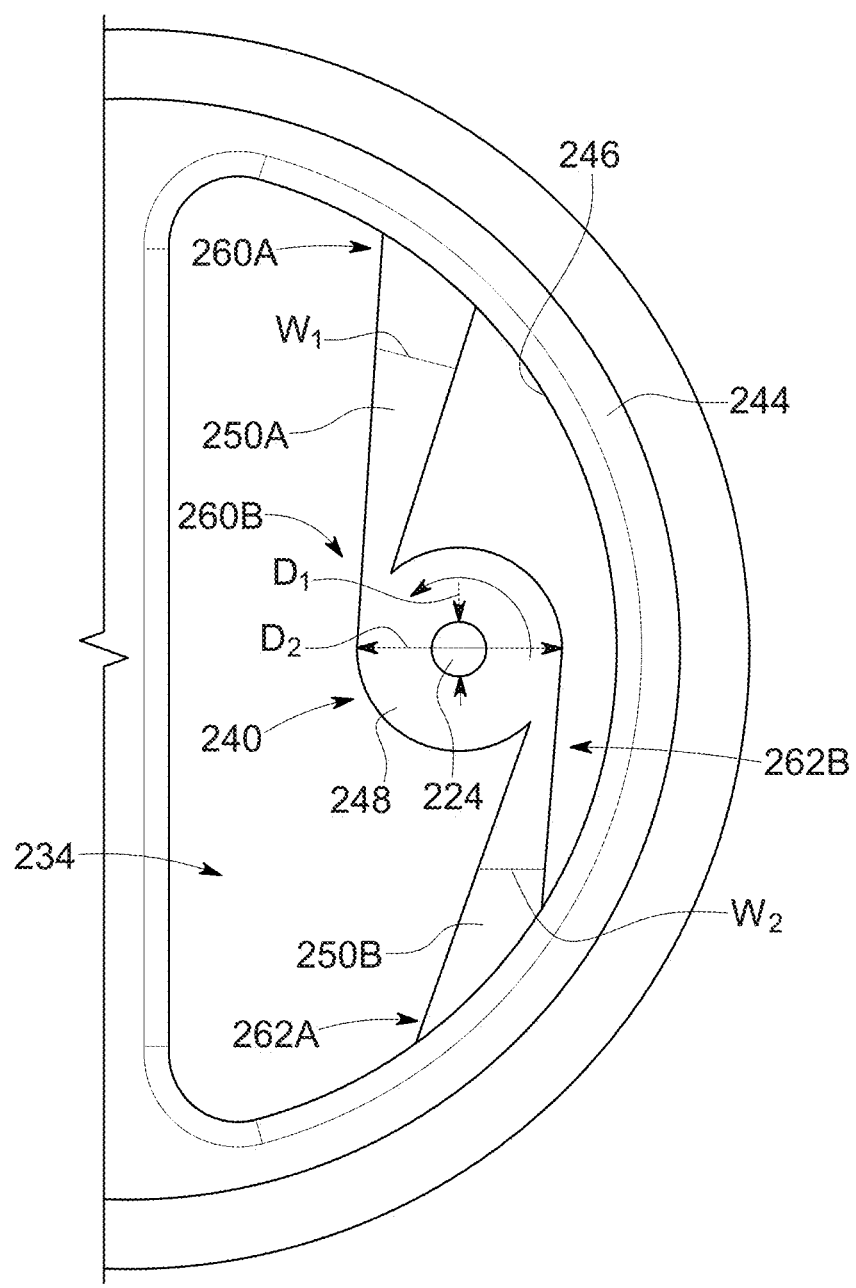
Figures 2, 8B:
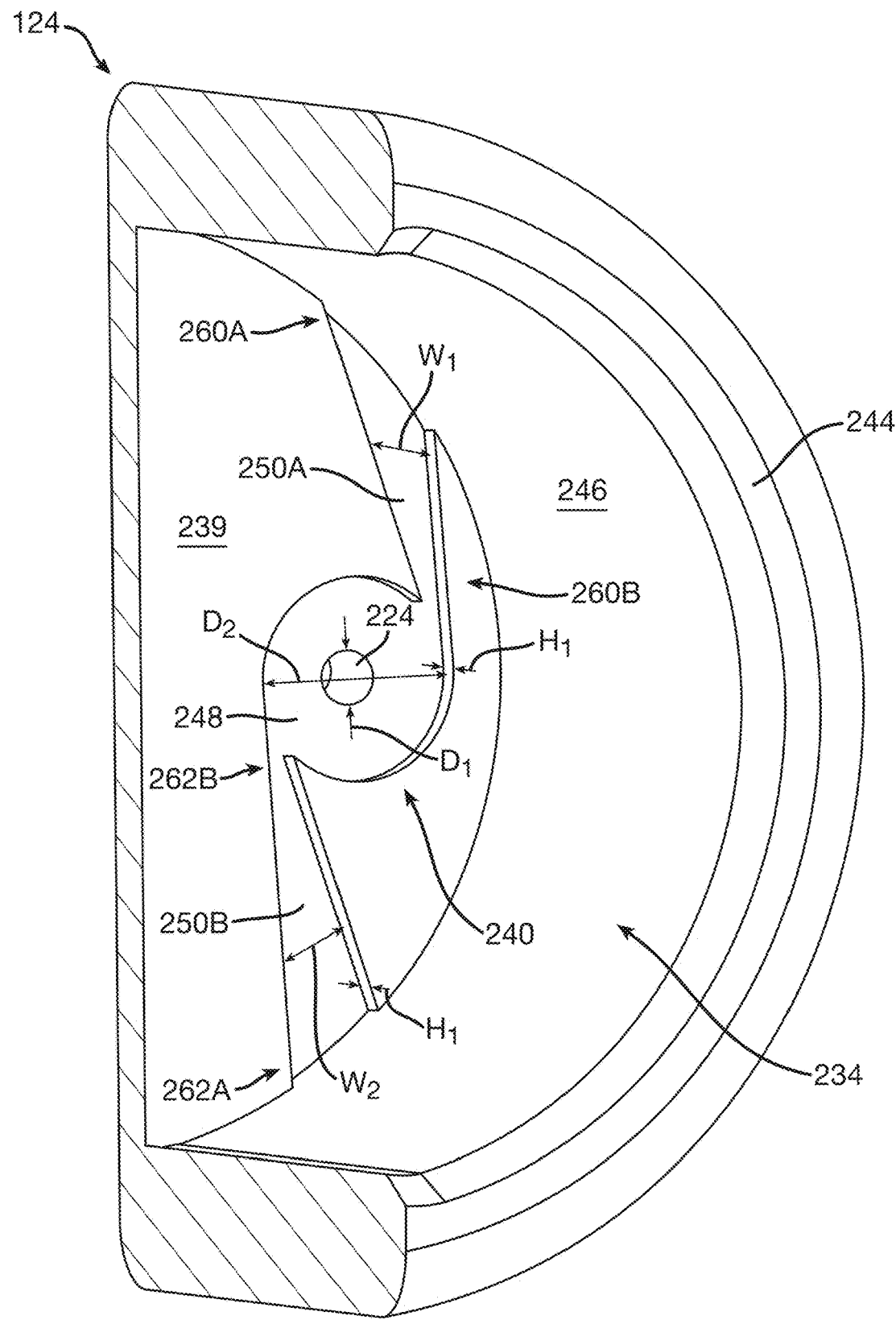
Figures 3, 8B:
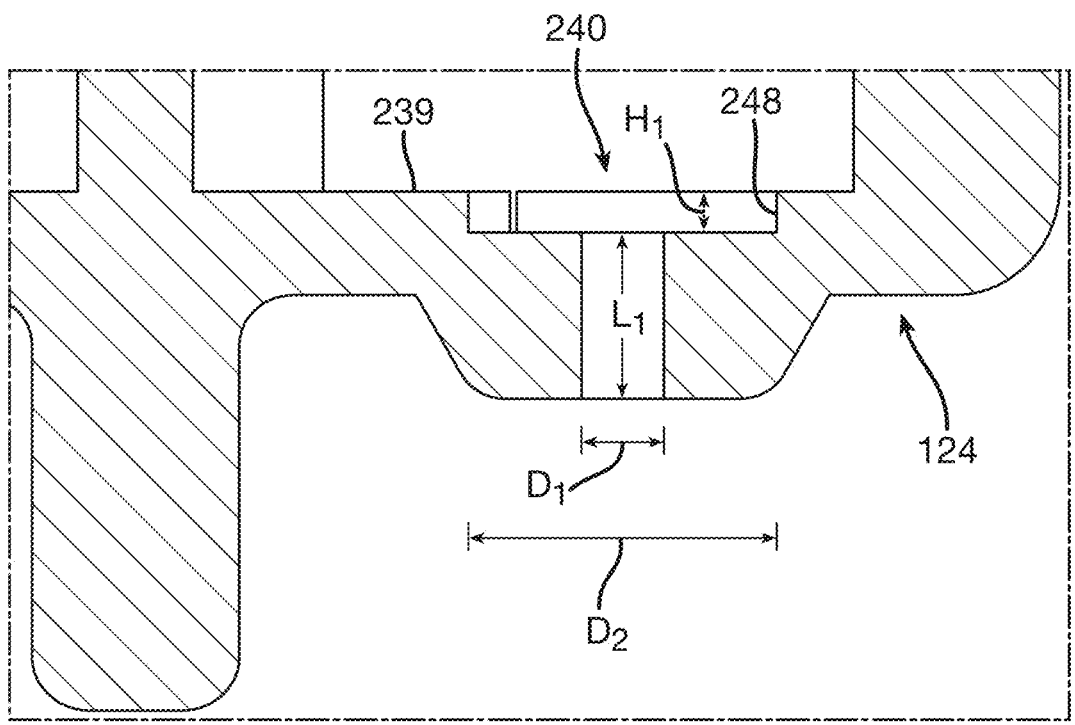

Referring to FIGS. 8B-1 and 8B-2, in one embodiment, the first spray opening 224 of the first fluid pathway 240 preferably defines a first diameter $D_1$ and the first swirl chamber 248 preferably defines a second diameter $D_2$ that is greater than the first diameter $D_1$ of the first spray opening 224. In one embodiment, the first spray opening 224 may be located in the center of the first swirl chamber 248. In one embodiment, a first one 250A of the first flutes desirably has an outer end 260A that is located adjacent the inner surface 246 of the outer peripheral wall 244 and an inner end 260B that is located adjacent the outer periphery of the first swirl chamber 248. In one embodiment, the first one 250A of the first flutes preferably has a width $W_1$ of about 0.005-0.010 inches that narrows between the outer end 260A and the inner end 260B thereof. In one embodiment, the narrowing of the first one 250A of the first flutes preferably increases the speed of the first fluid as it passes from the outer end 260A toward the inner end 260B of the first one 250A of the first flutes.

In one embodiment, a second one 250B of the first flutes desirably has an outer end 262A that is located adjacent the inner surface 246 of the outer peripheral wall 244 and an inner end 262B that is located adjacent the outer periphery of the first swirl chamber 248. In one embodiment, the first one 250B of the first flutes preferably has a width $W_2$ that narrows between the outer end 262A and the inner end 262B thereof. In one embodiment, the narrowing of the second one 250B of the first flutes preferably increases the speed of the first fluid as it passes from the outer end 262A toward the inner end 262B of the second one 250B of the first flutes.

Figures 4, 8B:
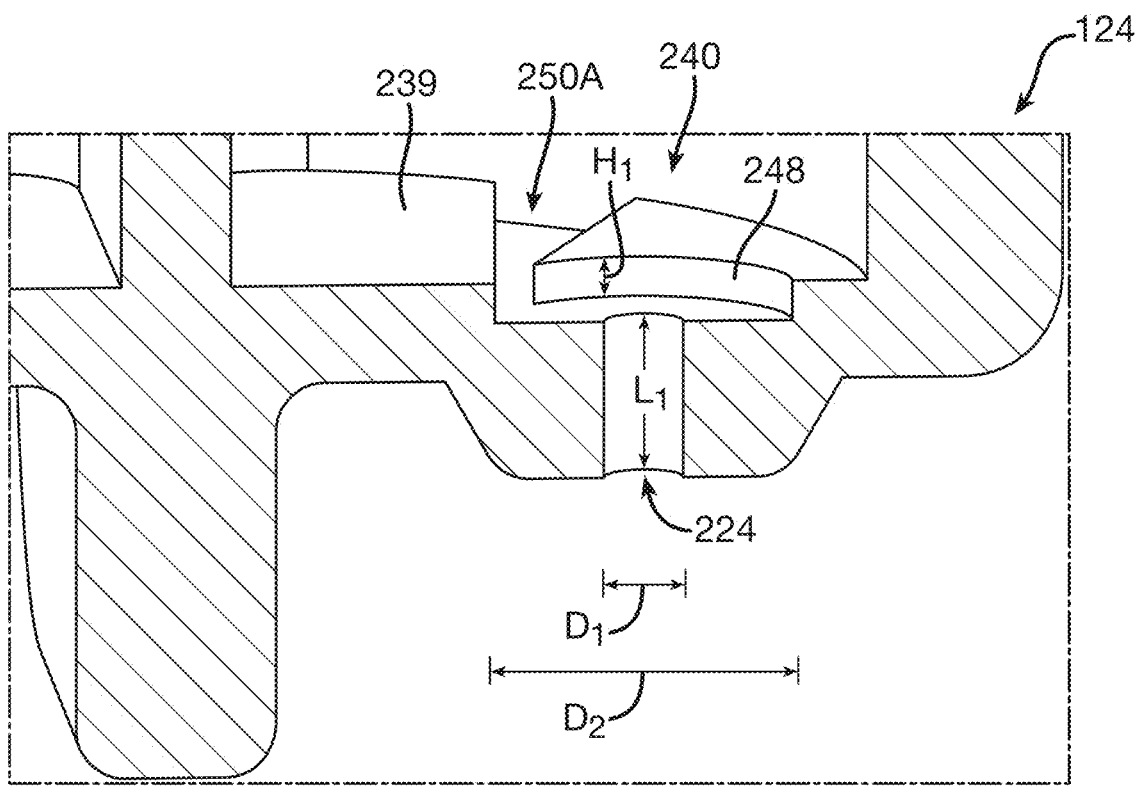

Referring to FIGS. 8B-2 through 8B-4, in one embodiment, the first fluid pathway 240 is formed in the inner surface 239 of the distal end wall 218 of the first D-shaped chamber 234 of the dispensing cap 124. In one embodiment, the first fluid pathway 240 including the first swirl chamber 248 and the first flutes 250A, 250B (FIG. 8B-1) define a height H1 of about 0.005-0.010 inches.

In one embodiment, the first spray opening 224 preferably has a diameter D1 that is less than the diameter D2 of the first swirl chamber 248. In one embodiment, the first spray opening preferably has a length L1 of about _____.

Figure 9:
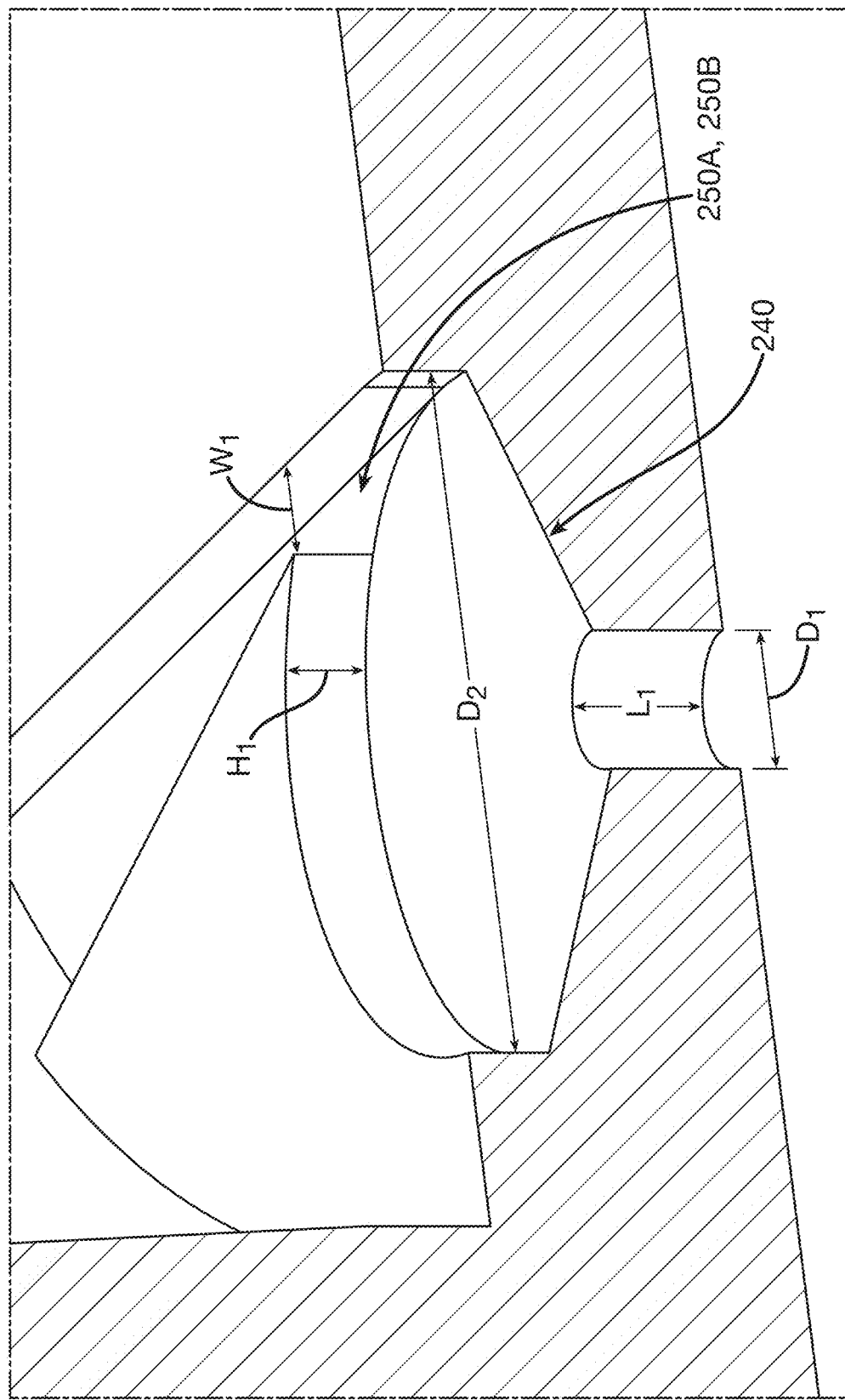
FIG. 9 is a schematic view of a first fluid pathway of a dispensing cap of a dispensing device, in accordance with one embodiment of the present patent application.

Referring to FIG. 9, in one embodiment, the dimensions of the first fluid pathway 240 may be modified to control the speed and/or the rate of rotation of the first fluid flowing through the first fluid pathway 240. Thus, one or more of the width and the height of the first flutes 250A, 250B may be modified to control the speed of the first fluid flowing through the first flutes. Moreover, the degree of narrowing of the first flutes 250A. 250B between the respective outer and inner ends thereof may be modified to control the speed of the first fluid flowing through the first flutes. In addition, the diameter D1, the height H1, and/or the chamfer of the first swirl chamber 248 may be modified to control the speed and/or the rate of rotation of the first fluid that is directed into the first spray opening 224. In one embodiment, the diameter D1 and the length L1 of the first spray opening 224 may be modified to control the speed and/or the dispensing angle of the first fluid as it is dispensed from the first spray opening.

Figure 10A:
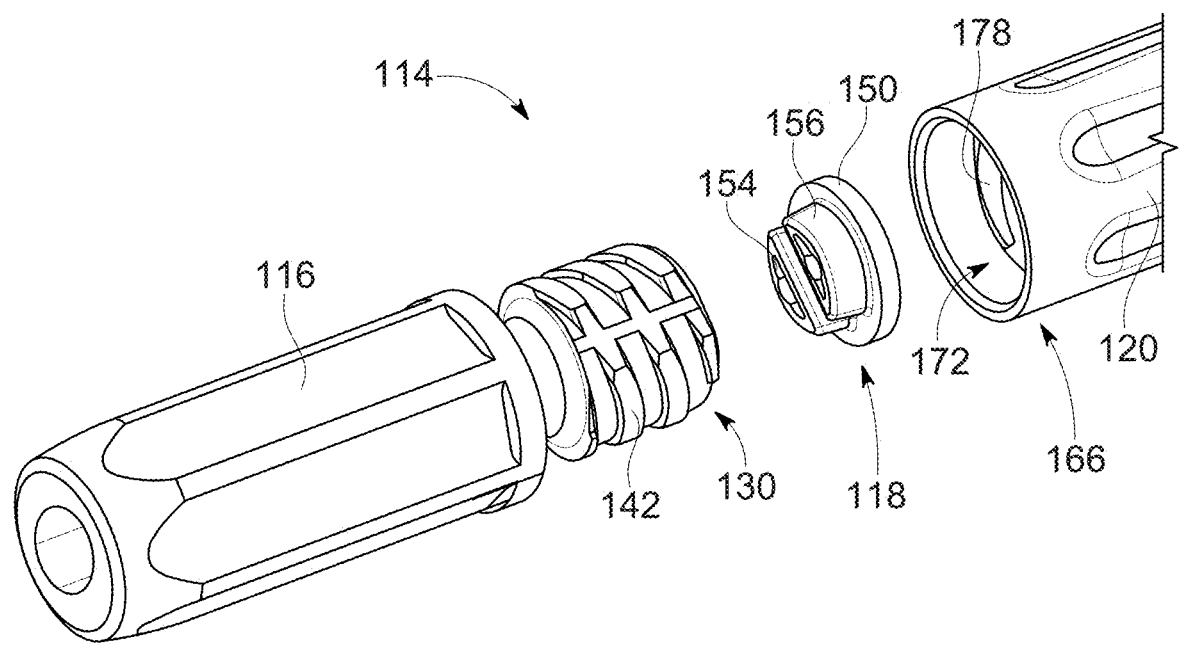
FIG. 10A is a perspective view of a method of assembling together the gasket and the tip housing shown in FIG. 2, in accordance with one embodiment of the present patent application.
Figure 10B:
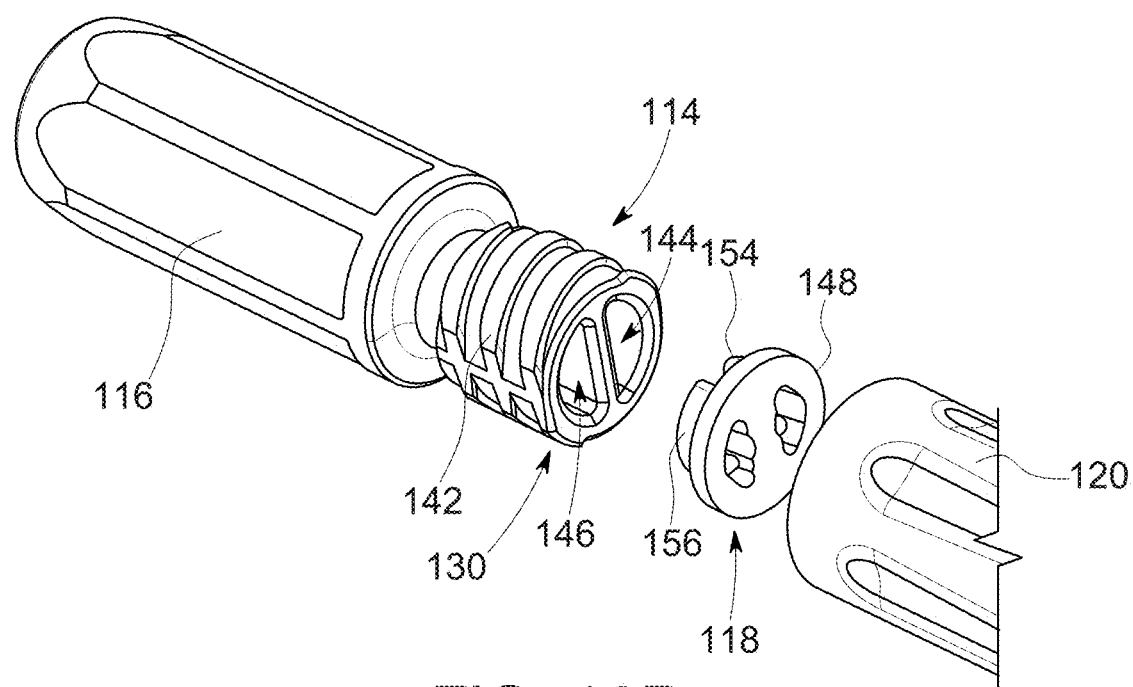
FIG. 10B is another perspective view of a method of assembling together the gasket and the tip housing shown in FIG. 2, in accordance with one embodiment of the present patent application.

Referring to FIGS. 10A and 10B, in one embodiment, the anti-clogging spray tip 114 may be assembled together by overmolding the gasket 118 onto the proximal end of the inner manifold 122. In one embodiment, after the gasket 118 is assembled to the proximal end of the inner manifold 122, the distal end of the gasket 118/inner manifold 122 subassembly may be inserted into the first opening 172 at the proximal end 166 of the tip housing 120 for assembling the gasket 116/inner manifold 122/tip housing 120 subassembly.

In one embodiment, the external threads 142 at the distal end 130 of the connector 116 are preferably threaded into the internal threads 178 located inside the proximal end of the tip housing 120 for securing the connector 116 with the tip housing 120.

In one embodiment, in order to assembly the anti-clogging spray tip 114 to the connector 116, the first and second D-shaped attachment plugs 154, 156 of the gasket 118 are desirably inserted into the respective D-shaped exit chambers 144, 146 at the distal end 130 of the connector 114. In one embodiment, the outer surfaces of the D-shaped attachment plugs 154, 156 preferably form a friction fit with the inner surfaces of the respective D-shaped exit chambers 144, 146.

Figure 11A:
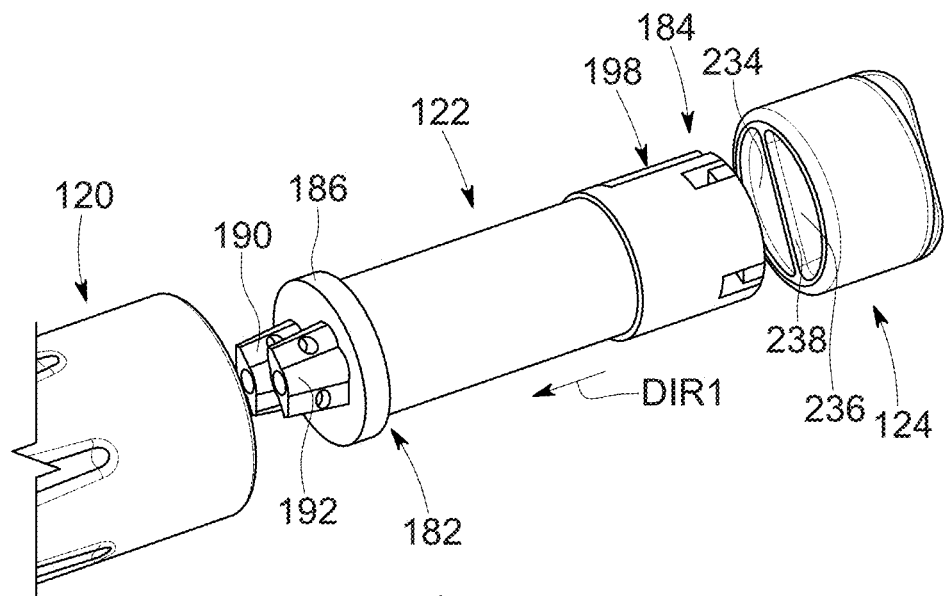
FIG. 11A is a perspective view of a method of assembling together the tip housing, the inner manifold, and the dispensing cap shown in FIG. 2, in accordance with one embodiment of the present patent application.
Figure 11B:
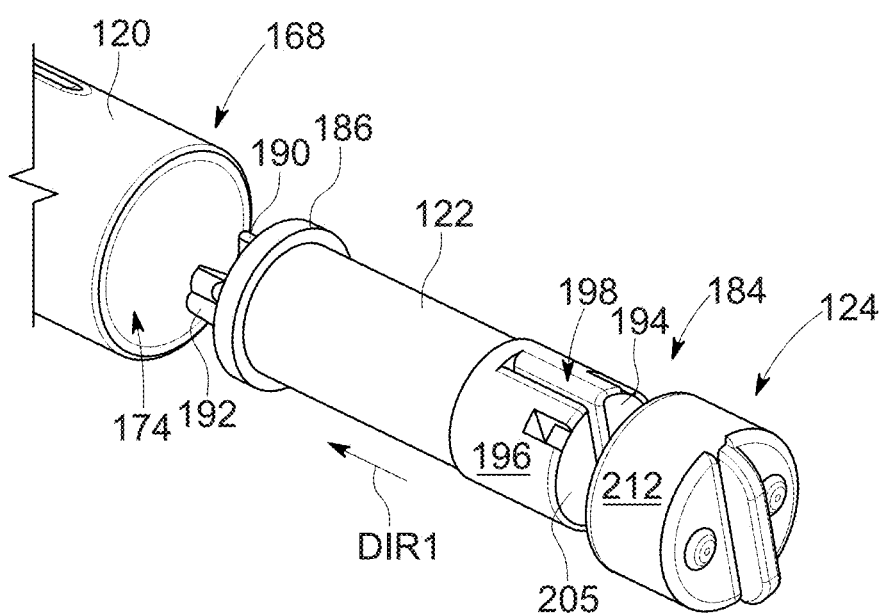
FIG. 11B is another perspective view of a method of assembling together the tip housing, the inner manifold, and the dispensing cap shown in FIG. 2, in accordance with one embodiment of the present patent application.

Referring to FIGS. 11A and 11B, in one embodiment, the inner manifold 122 may be assembled with the tip housing 120 by inserting the first and second butterfly-shaped connectors 190, 192 and the annular sealing flange 186 located at the proximal end 182 of the inner manifold 122 into the second opening 174 at the distal end 168 of the tip housing 120. In one embodiment, the inner manifold 122 is advanced in a proximal direction designated DIR1 until the first and second butterfly-shaped connectors 190, 192 are inserted into the respective butterfly-shaped openings 161, 163 formed in the distal end face 152 of the gasket 118 (FIG. 4B). In one embodiment, the outer surfaces of the first and second butterfly-shaped connectors 190, 192 preferably form a friction fit with the respective butterfly-shaped openings 161, 163 (FIG. 4B) of the gasket 118 for securing the proximal end of the inner manifold 122 with the connector 116/gasket 118/tip housing 120 subassembly (FIG. 10B).

In one embodiment, the dispensing cap 124 is preferably assembled with the distal end 184 of the inner manifold 122 by juxtaposing and/or aligning the interior dividing wall 238 of the dispensing cap 124 with the space 198 that extends between opposing inner walls of the first and second terminal chambers 194, 196 of the inner manifold 122.

In one embodiment, in order to assemble the dispensing cap 124 with the inner manifold 122, the first and second D-shaped chambers 234, 236 accessible on the proximal side of the dispensing cap 124 are juxtaposed with the respective first and second terminal chambers 194, 196 located at the distal end 184 of the inner manifold 122. In one embodiment, the dispensing cap 124 is advanced in the proximal direction DIR1 so that the interior dividing wall 238 of the dispensing cap 124 advances into the space 198 between the first and second terminal chambers 194, 196 of the inner manifold 122. The dispensing cap 124 is preferably advanced proximally until the end walls 239, 241 of the respective D-shaped chambers 234, 236 of the dispensing cap (FIG. 8A) abut against a distal face 205 (FIG. 11B) of the inner manifold 122.

In one embodiment, when the dispensing cap 124 is secured over the first and second terminal chambers 194, 196, the first radial openings 200A, 200B (FIG. 6F) of the first terminal chamber 194 (FIG. 6F) are preferably aligned with the outer ends of the first flutes 250A, 250B (FIG. 8A) of the dispensing cap 124, and the second radial openings 202A, 202B of the second terminal chamber 196 (FIG. 6F) are preferably aligned with the outer ends of the second flutes 256A, 256B (FIG. 8A) of the dispensing cap 124. In one embodiment, the first fluid of the multiple component material exits from the first terminal chamber via the first radial openings 200A, 200B (FIG. 6F) whereupon it is directed into the outer ends of the first flutes 250A, 250B (FIG. 8A). In one embodiment, the second fluid of the multiple component material exits from the second terminal chamber via the second radial openings 202A, 202B (FIG. 6F) whereupon it is directed into the outer ends of the second flutes 254A, 254B (FIG. 8A).

Figure 12A:
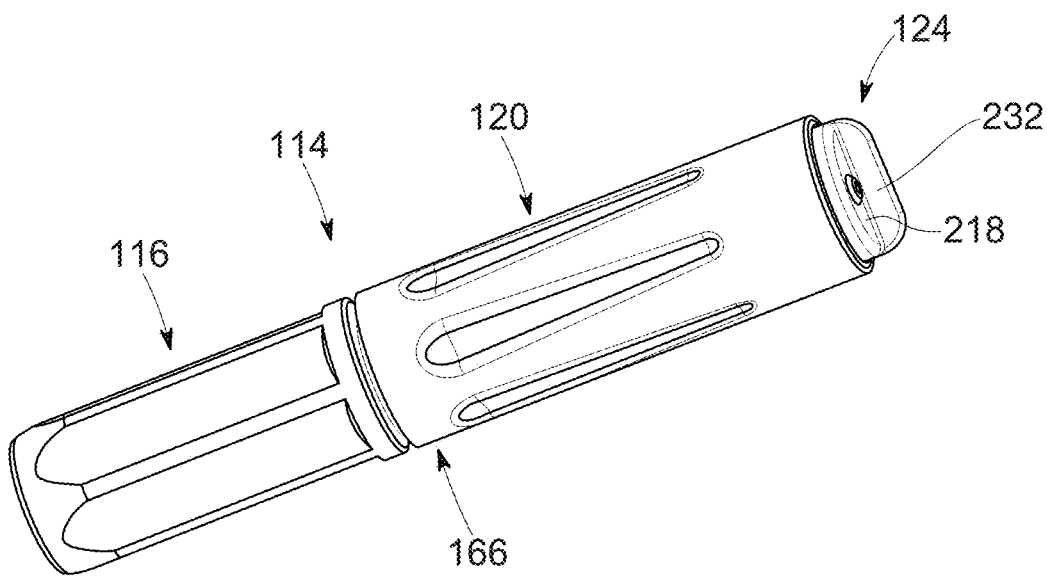
FIG. 12A is a side view of an anti-clogging spray tip used for spraying two fluids that react together, the anti-clogging spray tip being secured to a connector, in accordance with one embodiment of the present patent application.
Figure 12B:
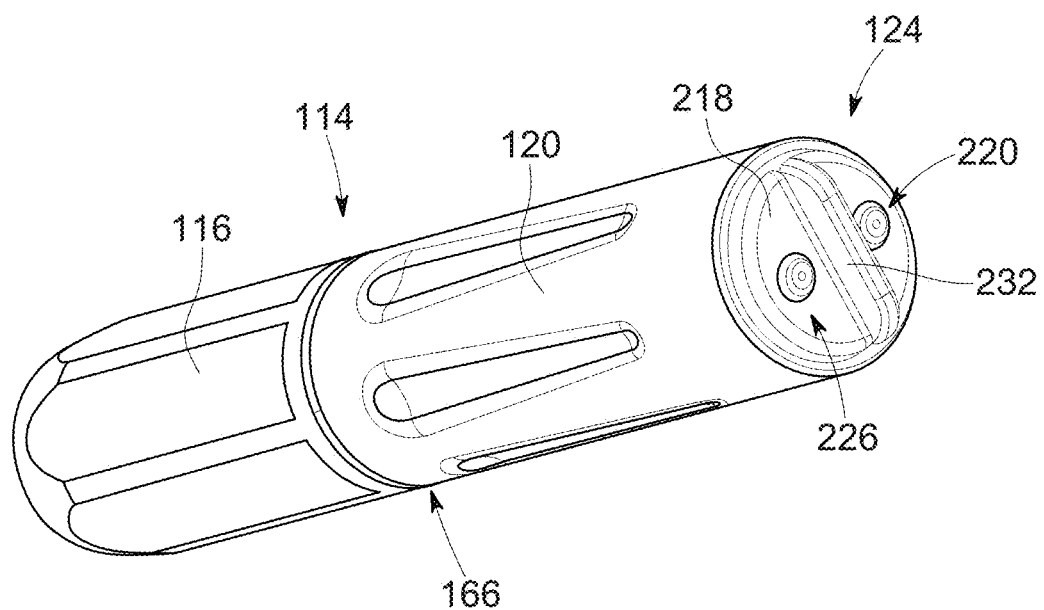
FIG. 12B is a perspective view of a distal end of the anti-clogging spray tip shown in FIG. 12A.

Referring to FIGS. 12A-12B, in one embodiment, the fully assembled anti-clogging spray tip 114 preferably includes the connector 116, which has a distal end with external threads that mesh with internal threads located at the proximal end of the tip housing 120. The gasket 118 (FIG. 2) is preferably disposed between the distal end of the connector 116 and the tip housing 120. In one embodiment, the proximal end 166 of the tip housing 120 preferably surrounds the gasket. The anti-clogging spray tip 114 desirably includes the dispensing cap 124 that is accessible at the distal-most end of the anti-clogging spray tip 114. The inner manifold 122 (FIG. 2) is preferably disposed within the tip housing 120 and extends between the distal end of the connector 116 and the dispensing cap 124. The exterior dividing wall 232 of the dispensing cap 124, which projects distally from the distal end face 218 of the dispensing cap 124, provides a barrier that separates the first raised mound 220 from the second raised mound 226 so that the first and second fluids that are sprayed from the respective first and second raised mounds do not mix with one another over the distal end face 218, which minimizes the likelihood of the first and second raised mounds becoming clogged during a spraying operation.

Figure 13:
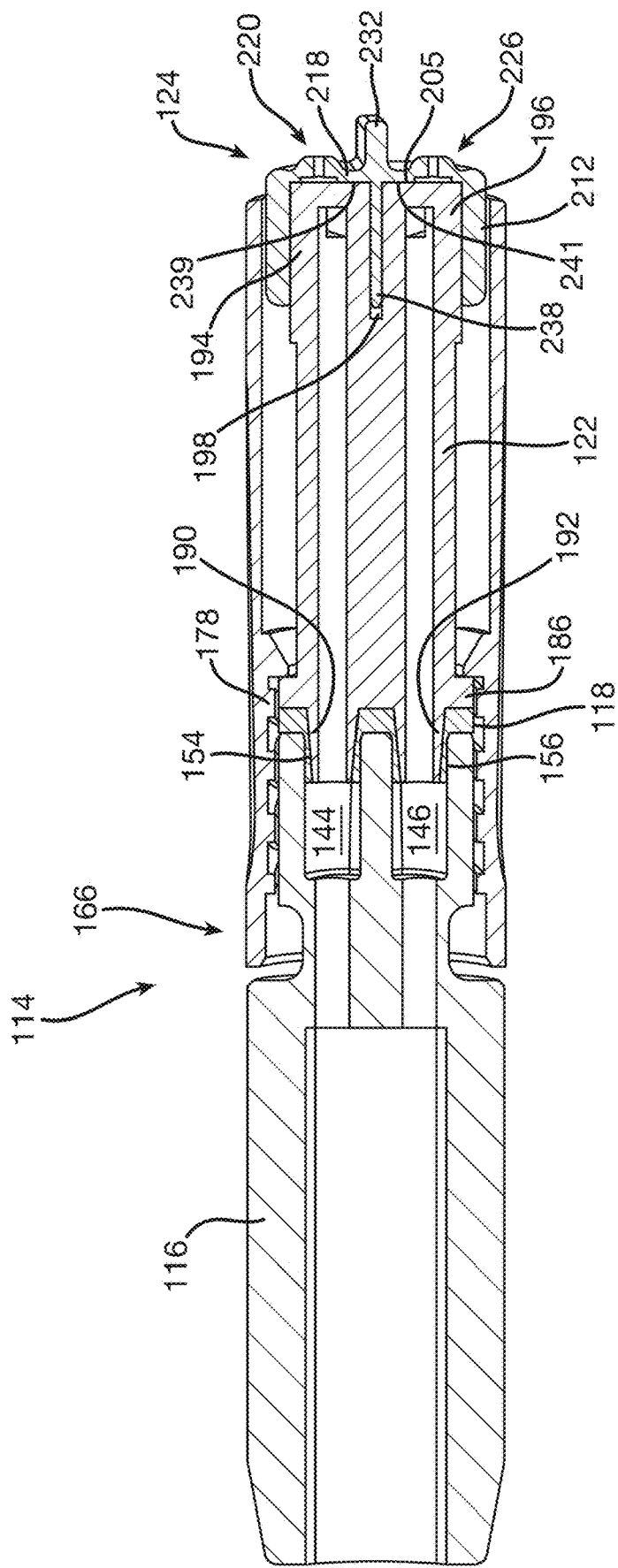
FIG. 13 is a cross-sectional view of the anti-clogging spray tip shown in FIGS. 12A and 12B.
Figure 14:
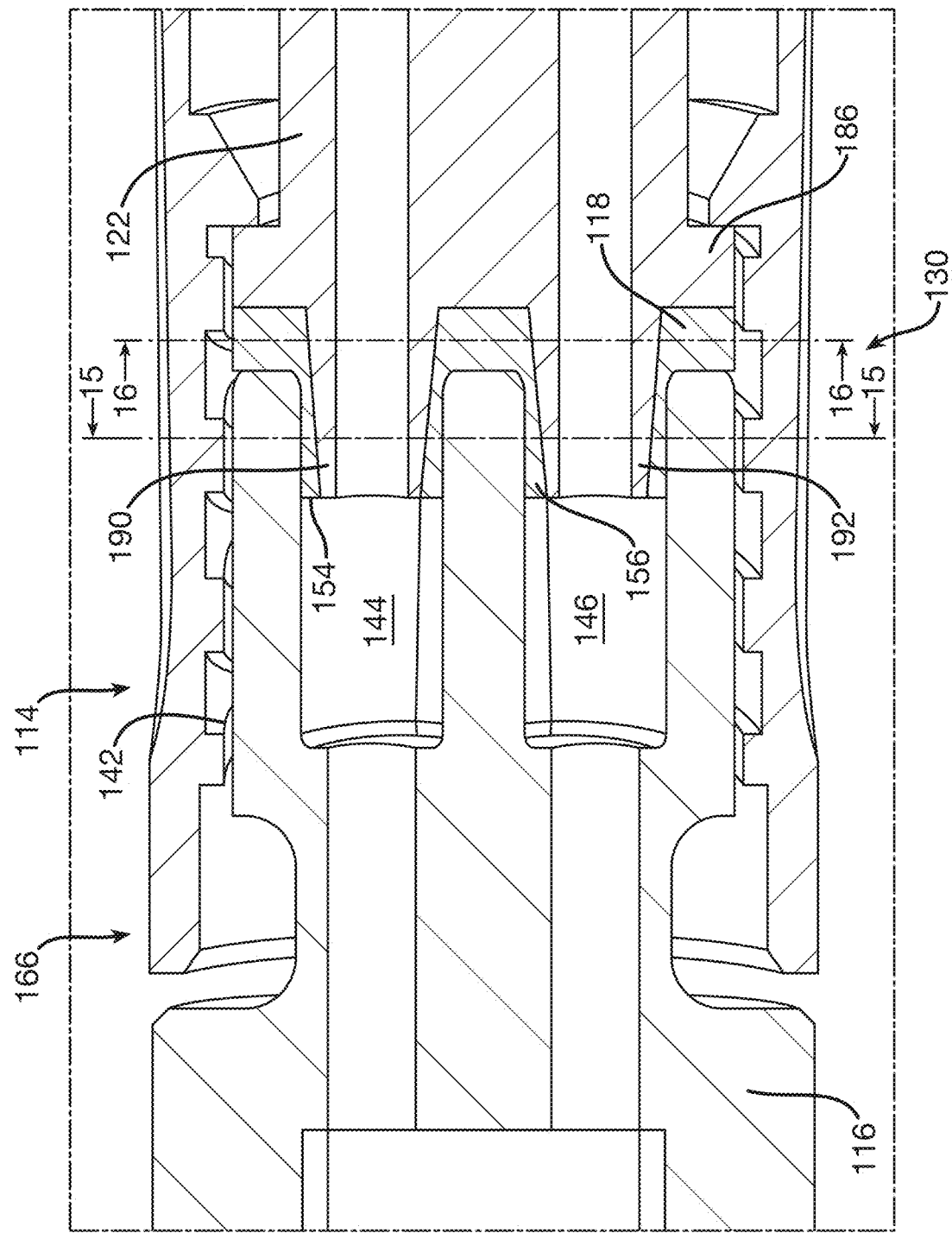
FIG. 14 is a magnified cross-sectional view of a mid-section of the anti-clogging spray tip shown in FIG. 13.

Referring to FIGS. 13 and 14, in one embodiment, the anti-clogging spray tip 114 preferably includes the distal end 130 of the connector 116 inserted into the opening at the proximal end 166 of the tip housing 120. The external threads 142 (FIG. 3A) at the distal end 130 of the connector 116 are desirably threaded into the internal threads 178 located inside the proximal end 166 of the tip housing 120 for securing the connector 116 and the tip housing 120 to one another. The gasket 118 is desirably juxtaposed between the distal end 130 of the connector 116 and the annular sealing flange 186 of the inner manifold 122. The D-shaped attachment plugs 154, 156 of the gasket 118, which preferably project proximally from a proximal end face of the annular plate 148 of the gasket 118, are inserted into the respective D-shaped exit chambers 144, 146 (FIG. 3C) located at the distal end 130 of the connector 116 for securing the gasket 118 to the distal end of the connector. In one embodiment, the annular plate 148 of the gasket 118 is preferably juxtaposed between the distal end 130 of the connector 116 and the annular sealing flange 186 located at the proximal end 182 of the inner manifold 122. The first and second butterfly-shaped connectors 190, 192, projecting proximally from the proximal end of the inner manifold 122, are preferably inserted into the butterfly shaped openings formed in the distal end face 152 (FIG. 4B) of the gasket 118 for assembling the proximal end of the inner manifold 122 with the gasket 118.

Figure 15:
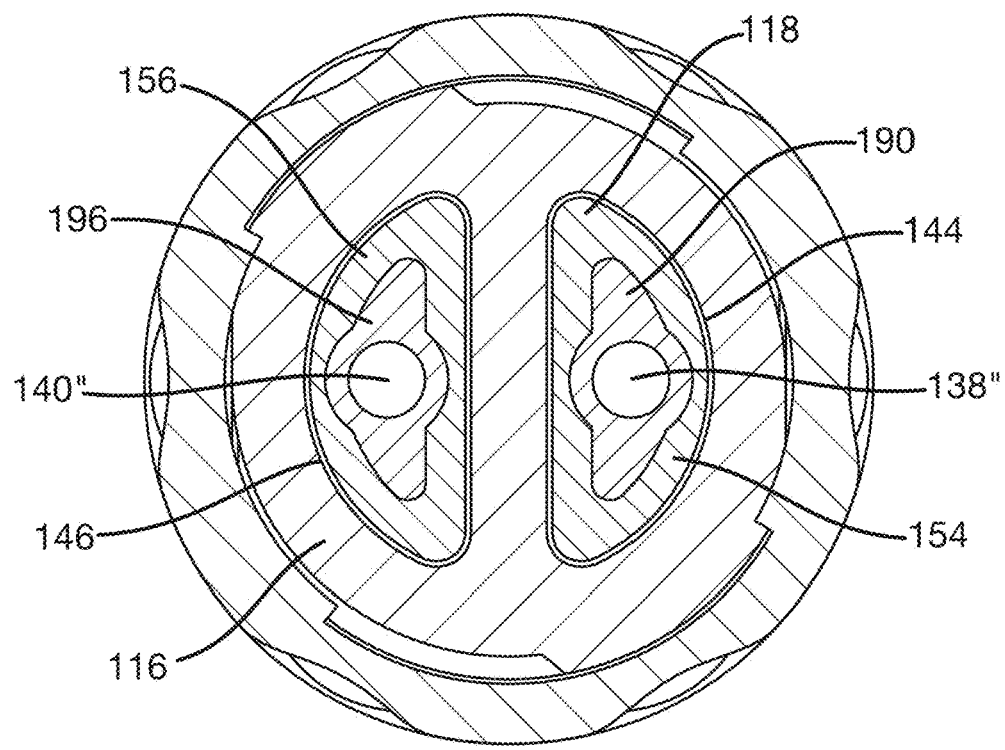
FIG. 15 is a cross-sectional view of the anti-clogging spray tip of FIG. 14 taken along line 15-15 of FIG. 14.

Referring to FIG. 15, in one embodiment, in order to secure the gasket 118 (FIG. 2) with the connector 116, the D-shaped attachment plugs 154, 156 of the gasket 118 (FIG. 11A) are preferably inserted into the respective D-shaped exit chambers 144, 146 of the connector 116 (FIG. 11B), whereupon the outer surfaces of the D-shaped attachment plugs 154, 156 of the gasket 118 preferably form a friction fit with the inner surfaces of the respective D-shaped exit chambers 144, 146 of the connector 116. The first butterfly-shaped connector 190 of the inner manifold 122 (FIG. 2) preferably includes a first lumen 138" that is adapted to receive a first cannula that contains a first fluid of a multiple component material. The second butterfly-shaped connector 192 of the inner manifold 122 (FIG. 2) preferably includes a second lumen 140" that is adapted to receive a second cannula that contains a second fluid of a multiple component material.

Figure 16:
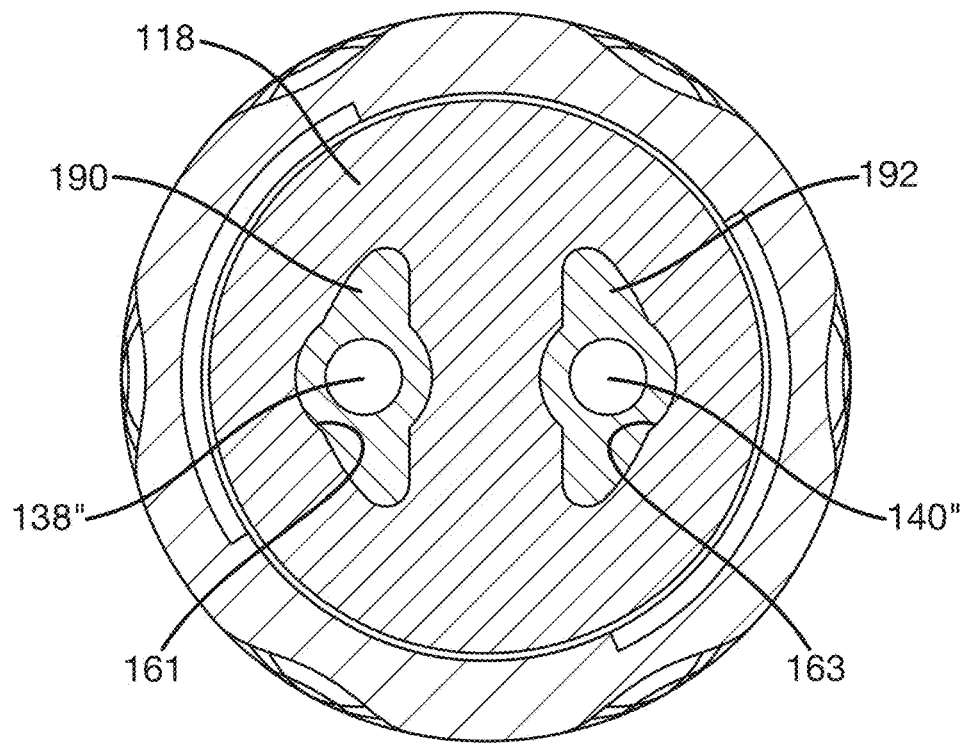
FIG. 16 is a cross-sectional view of the anti-clogging spray tip shown in FIG. 14 taken along line 16-16 of FIG. 14.

Referring to FIG. 16, in one embodiment, in order to secure the proximal end of the inner manifold 122 with the gasket 118 (FIG. 2), the outer surfaces of the first and second butterfly-shaped connectors 190, 192 of the inner manifold are preferably inserted into the butterfly-shaped openings 161, 163 (FIG. 4B) formed in the distal face of the gasket 118, whereupon the outer surfaces of the first and second butterfly-shaped connectors 190, 192 form a friction fit with the respective butterfly-shaped openings of the gasket 118. The first butterfly-shaped connector 190 preferably includes a first lumen 138" that is adapted to receive a first cannula that contains a first fluid of a multiple component material. The second butterfly-shaped connector 192 preferably includes a second lumen 140" that is adapted to receive a second cannula that contains a second fluid of a multiple component material.

Figure 17:
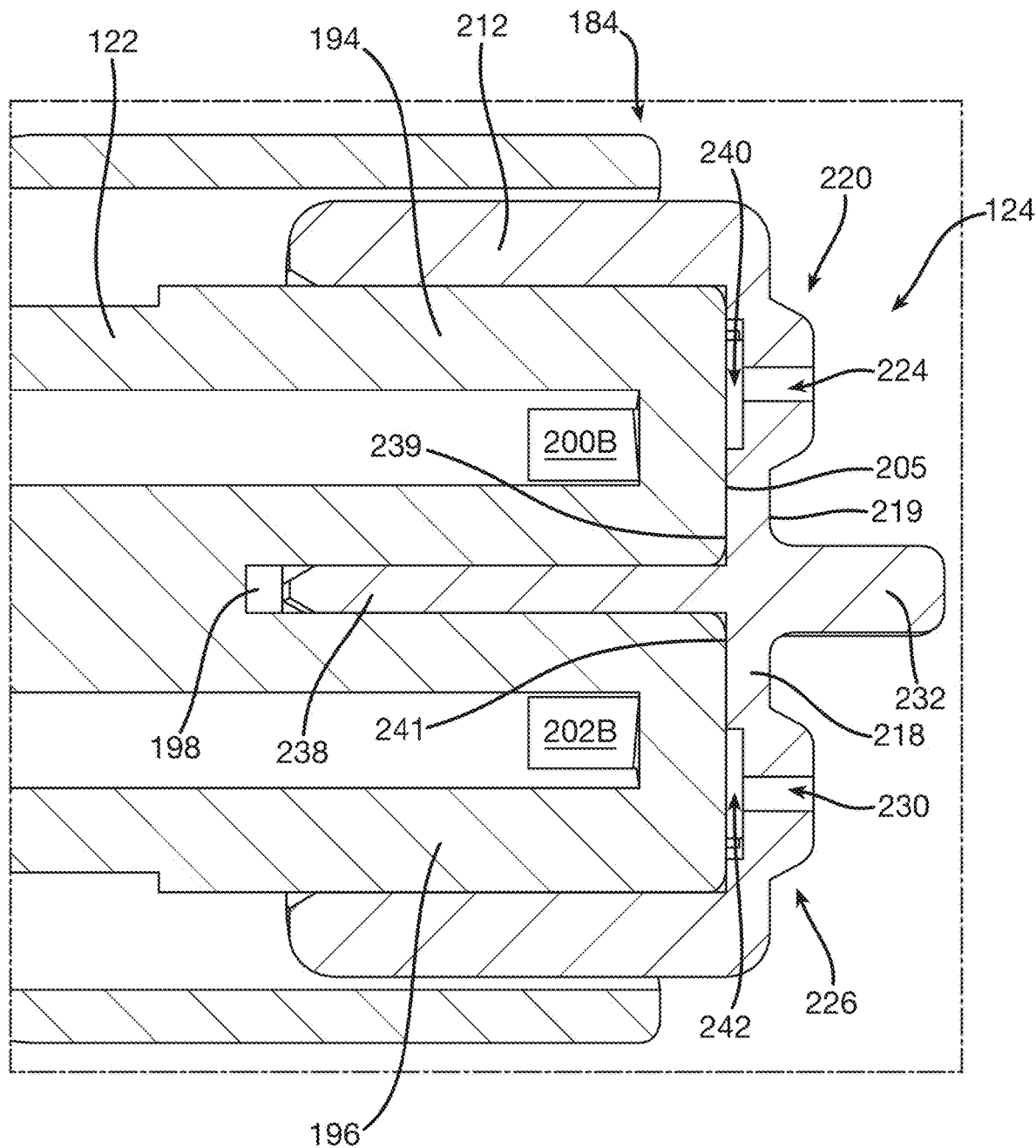
FIG. 17 is a cross-sectional view of a distal end of the anti-clogging spray tip shown in FIG. 13.

Referring to FIGS. 13 and 17, in one embodiment, the internal dividing wall 238 of the dispensing cap 124 is preferably inserted into the space 198 that divides the first and second terminal chambers 194, 196 of the inner manifold 122 from one another. In one embodiment, the internal dividing wall 238 preferably forms a friction fit with the distal end 184 of the inner manifold 122 for securing the dispensing cap 124 and the inner manifold 122 together. In one embodiment, the inner surfaces 239, 241 (FIG. 7C) of the distal end wall 218 of the respective first and second D-shaped chambers 234, 236 (FIG. 7C) of the dispensing cap preferably engage the distal end wall 205 (FIG. 11B) of the inner manifold 122. The tubular member 212 of the dispensing cap 124 preferably surrounds the outer surfaces of the respective first and second terminal chambers 194, 196 of the inner manifold 122. The exterior dividing wall 232 of the dispensing cap 124 preferably projects distally from the distal face 219 of the distal end wall 218 of the dispensing cap 124 for acting as a barrier that separates the respective first and second raised orifices 220, 226 from one another.

Referring to FIG. 17, in one embodiment, the first terminal chamber 194 of the inner manifold 122 preferably includes first radial openings 200A, 200B (FIG. 6F) that directs the first fluid of the multi-component material out of the first terminal chamber 194 and into the first fluid pathway 240 of the dispensing cap 124 (FIG. 8A) whereupon the first fluid is swirled within the first fluid pathway prior to being sprayed from the first spray opening 224 of the first raised orifice 220 of the dispensing cap 124. The second terminal chamber 196 of the inner manifold 122 preferably includes second radial openings 202A, 202B (FIG. 6F) that direct the second fluid of the multi-component material out of the second terminal chamber 196 and into the second fluid pathway 242 of the dispensing cap 124 (FIG. 8A) whereupon the second fluid is swirled within the second fluid pathway prior to being sprayed from the second spray opening 230 of the second raised orifice 226 of the dispensing cap 124.

The external dividing wall 232 of the dispensing cap 124 projects distally from the distal surface 219 of the distal end wall 218 of the dispensing cap 124 to insure that the first and second fluids of the multi-component material do not mix on the distal surface 219 of the distal end wall 218, which may result in clogging of the first spray opening 224 of the first raised orifice 220 and/or the second spray opening 230 of the second raised orifice 226.

Figure 18:
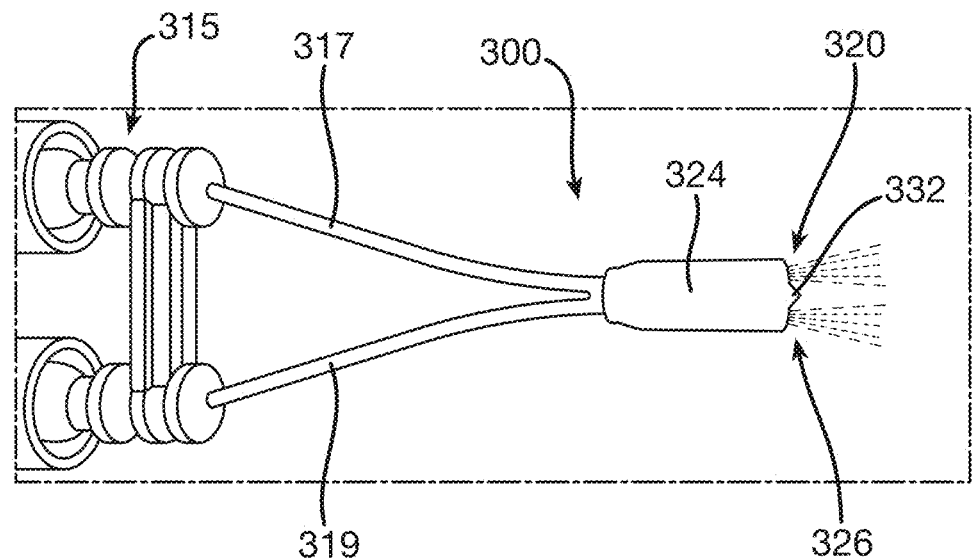
FIG. 18 is a top plan view of a dispensing device having an anti-clogging spray tip that sprays two fluids that react together, in accordance with one embodiment of the present patent application.

Referring to FIG. 18, in one embodiment, a dispensing device 300 preferably includes a manifold 315 that directs the first and second fluids of a multi-component material through first and second cannulas 317, 319, respectively, toward an anti-clogging spray tip 324 that is constructed as disclosed herein. The anti-clogging spray tip 324 has a distally extending exterior dividing wall 332 that preferably divides and separates first and second raised mounds 320, 326 from one another. The first and second fluids may be sprayed from the respective first and second raised orifices 320, 326 whereupon the first and second fluids mix together for reacting with one another.

Figure 19:
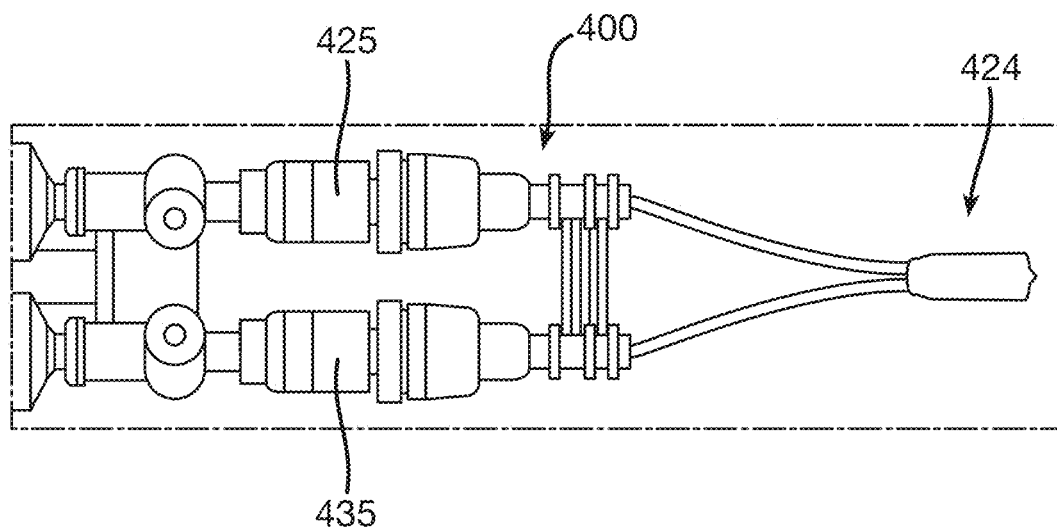
FIG. 19 is a top plan view of a dispensing device having an anti-clogging spray tip that sprays two fluids that react together, in accordance with one embodiment of the present patent application.

Referring to FIG. 19, in one embodiment, a dispensing device 400 may be similar to that shown and described herein and preferably includes first and second one way check valves 425, 435 associated with each of the first and second fluids of a multiple component material to prevent back flow of the first and second fluids, which could result in clogging of the anti-clogging spray tip 424.

In one embodiment, the spray tips disclosed herein preferably include first and second fluid paths, which are adapted to receive the components (e.g., a first fluid and a second fluid) of a tissue sealant and/or other biological adhesive materials. In one embodiment, the tissue sealants and/or other biologic adhesive materials are preferably used for closing incisions at surgical sites. In one embodiment, the tissue sealants may include fibrin, which is comprised of thrombin, and a fibrinogen material, although other tissue sealing and tissue adhesive formulations may also be used.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A spray tip for dispensing fluids that react together comprising:
    a first lumen for a first fluid;
    a second lumen for a second fluid;
    a dispensing cap located at distal ends of said respective first and second lumens and defining a distal end of said spray tip, said dispensing cap comprising:
        a distal end wall defining a closed end of said dispensing cap;
        a first spray orifice formed in said distal end wall that is in fluid communication with said first lumen;
        a second spray orifice formed in said distal end wall that is in fluid communication with said second lumen; and an external dividing wall that is integrally formed with said distal end wall of said dispensing cap and that projects distally from said distal end wall of said dispensing cap and that extends distally and across the outer surface of said distal end wall of said dispensing cap and between said first and second spray orifices for forming a barrier between said first and second spray orifices, wherein said first spray orifice includes a first raised mound that projects distally from an outer surface of said distal end wall of said dispensing cap, wherein said second spray orifice includes a second raised mound that projects distally from the outer surface of said distal end wall of said dispensing cap, wherein said external dividing wall has a proximal end that is secured to the outer surface of said distal end wall and a distal, free end that is distal to respective first and second apexes of said first and second raised mounds for defining a distal-most end of said dispensing cap, wherein said first fluid and said second fluid chemically react together for the first time only after being dispensed from said respective first and second spray orifices and flowing distally beyond the distal end of the external dividing wall, wherein said dispensing cap further comprises:
a cylindrical shaped body having a proximal end that is open for coupling with the distal ends of said first and second lumens and a distal end that is closed by said distal end wall; and
an internal dividing wall located inside said cylindrical shaped body that extends between the proximal end of said cylindrical shaped body and said distal end wall for dividing an interior region of said dispensing cap into a first chamber that is in fluid communication with said first lumen through a first radial opening and a second chamber that is in fluid communication with said second lumen through a second radial opening.

2. The spray tip as claimed in claim 1, wherein said first and second raised mounds of said respective first and second spray orifices comprise hydrophobic surfaces adapted for repelling fluids.

3. The spray tip as claimed in claim 1, wherein said external dividing wall projects distally from an outer surface of said distal end wall of said dispensing cap, and wherein said external dividing wall extends completely across the outer surface of said distal end wall of said dispensing cap for preventing said first and second fluids dispensed from said first and second respective spray orifices from contacting one another over the outer surface of said distal end wall of said dispensing cap.

4. The spray tip as claimed in claim 1, wherein said first mound comprises said first apex and a first sloping surface that slopes outwardly between said first apex and the outer surface of said distal wall of said dispensing cap, and wherein said second mound comprises said second apex and a second sloping surface that slopes outwardly between said second apex and the outer surface of said distal wall of said dispensing cap.

5. The spray tip as claimed in claim 1, wherein said distal end wall of said dispensing cap has an inner surface, and wherein said internal dividing wall has a distal end that is secured to the inner surface of said distal end wall for dividing the inner surface of said distal end wall of said dispensing cap into a first region that is disposed within said first chamber and a second region that is disposed within said second chamber.

6. The spray tip as claimed in claim 5, further comprising:
a first fluid pathway formed in the first region of the inner surface of said distal end wall of said dispensing cap, wherein said first fluid pathway is in fluid communication with said first spray orifice; and
a second fluid pathway formed in the second region of the inner surface of said distal end wall of said dispensing cap, wherein said second fluid pathway is in fluid communication with said second spray orifice.

7. The spray tip as claimed in claim 6, wherein said first fluid pathway comprises:
a first swirl chamber that is in fluid communication with said first spray orifice; and
a pair of first flutes that extend radially outward from said first swirl chamber.

8. The spray tip as claimed in claim 7, wherein said second fluid pathway comprises:
a second swirl chamber that is in fluid communication with said second spray opening; and
a pair of second flutes that extend radially outward from said second swirl chamber.

9. The spray tip as claimed in claim 8, further comprising:
said first lumen containing said first fluid that is directed into said first fluid pathway of said dispensing cap, wherein said first swirl chamber is configured to rotate said first fluid prior to dispensing said first fluid from said first spray orifice; and
said second lumen containing said second fluid that is directed into said second fluid pathway of said dispensing cap, wherein said second swirl chamber is configured to rotate said second fluid prior to dispensing said second fluid from said first spray orifice.

10. The spray tip as claimed in claim 9, further comprising:
a first syringe containing the first fluid;
a second syringe containing the second fluid;
a first one-way check valve located downstream from said first syringe and being in fluid communication with said first lumen; and
a second one-way check valve located downstream from said second syringe and being in fluid communication with said second lumen.

11. The spray tip as claimed in claim 8, wherein said first flutes extend away from one another on opposite sides of said first swirl chamber, and wherein said second flutes extend away from one another on opposite sides of said second swirl chamber.

12. A spray tip for dispensing fluids that react together comprising:
a first lumen for a first fluid;
a second lumen for a second fluid;
a dispensing cap located at distal ends of said respective first and second lumens, said dispensing cap comprising:
a cylindrical shaped body having a proximal end that is open for receiving distal ends of said first and second lumens and a distal end that is closed by a distal end wall;
a first spray orifice formed in said distal end wall that is in fluid communication with said first lumen, wherein said first spray orifice includes a first raised mound that projects distally from an outer surface of said distal end wall of said dispensing cap;
a second spray orifice formed in said distal end wall that is in fluid communication with said second lumen, wherein said second spray orifice includes a second raised mound that projects distally from the outer surface of said distal end wall of said dispensing cap;

an external dividing wall that is integrally formed with said distal end wall of said dispensing cap and that projects distally from the outer surface of said distal end wall of said dispensing cap, wherein said external dividing wall extends distally and across the outer surface of said distal end wall of said dispensing cap and between said first and second spray orifices for forming a barrier between said first and second spray orifices at the outer surface of said distal end wall of said dispensing cap, wherein said first fluid and said second fluid chemically react together for the first time only after being dispensed from said respective first and second spray orifices and flowing distally beyond the distal end of the external dividing wall, wherein said dispensing cap further comprises:

an internal dividing wall located inside said cylindrical shaped body that extends between the proximal end of said cylindrical shaped body and an inner surface of said distal end wall for dividing an interior region of said dispensing cap into a first chamber that is in fluid communication with said first lumen through a first radial opening and a second chamber that is in fluid communication said second lumen through a second radial opening.

13. The spray tip as claimed in claim 12, wherein the first chamber is in fluid communication with the distal end of said first lumen and the second chamber is in fluid communication with the distal end of said second lumen.

14. The spray tip as claimed in claim 13, further comprising:

a first fluid pathway formed in a first region of the inner surface of said distal end wall of said dispensing cap, wherein said first fluid pathway is in fluid communication with the distal end of said first lumen and said first spray orifice; and a second fluid pathway formed in a second region of the inner surface of said distal end wall of said dispensing cap, wherein said second fluid pathway is in fluid communication with the distal end of said second lumen and said second spray orifice.

15. The spray tip as claimed in claim 14, wherein said first fluid pathway comprises:

a first swirl chamber that is formed in the inner surface of said distal end wall and that is in fluid communication with said first spray orifice; and a pair of first flutes that are formed in the inner surface of said distal end wall and that extend radially outward from said first swirl chamber to an outer perimeter of the inner surface of said distal end wall of said dispensing cap, wherein each of said first flutes has a width.

16. The spray tip as claimed in claim 15, wherein said second fluid pathway comprises:

a second swirl chamber that is formed in the inner surface of said distal end wall and that is in fluid communication with said second spray opening; and a pair of second flutes that are formed in the inner surface of said distal end wall and that extend radially outward from said second swirl chamber to an outer perimeter of the inner surface of said distal end wall of said dispensing cap, wherein each of said second flutes has a width.

17. The spray tip as claimed in claim 16, wherein said first flutes extend from an inner surface of said cylindrical shaped body to an outer perimeter of said first swirl chamber, and wherein said second flutes extend from the inner surface of said cylindrical shaped body to an outer perimeter of said second swirl chamber.

18. The spray tip as claimed in claim 12, wherein said external dividing wall has a proximal end that is secured to the outer surface of said distal end wall and a distal, free end that is distal to respective apexes of said first and second raised mounds for defining a distal-most end of said dispensing cap.

19. A spray tip for dispensing fluids that react together comprising:

a first lumen for a first fluid;

a second lumen for a second fluid;

a dispensing cap located at distal ends of said first and second lumens, said dispensing cap comprising:

a cylindrical shaped body having a proximal end that is open for being coupled with the distal ends of said first and second lumens and a distal end that is closed by a distal end wall having an inner surface and an outer surface;

a first spray orifice formed in said distal end wall that is in fluid communication with the distal end of said first lumen, wherein said first spray orifice includes a first raised mound that projects distally from the outer surface of said distal end wall of said dispensing cap;

a second spray orifice formed in said distal end wall that is integrally formed with said distal end wall of said dispensing cap and that is in fluid communication with the distal end of said second lumen, wherein said second spray orifice includes a second raised mound that projects distally from the outer surface of said distal end wall of said dispensing cap;

an external dividing wall that projects distally from the outer surface of said distal end wall of said dispensing cap, wherein said external dividing wall extends distally and across the outer surface of said distal end wall of said dispensing cap and between said first and second spray orifices for forming a barrier between said first and second spray orifices, wherein said first fluid and said second fluid chemically react together for the first time only after being dispensed from said respective first and second spray orifices and flowing distally beyond the distal end of the external dividing wall, wherein said dispensing cap further comprises:

an internal dividing wall located inside said cylindrical shaped body that extends between the proximal end of said cylindrical shaped body and said distal end wall for dividing an interior region of said dispensing cap into a first chamber that is in fluid communication with said first lumen through a first radial opening and a second chamber that is in fluid communication with said second lumen through a second radial opening.

20. The spray tip as claimed in claim 19, wherein said dispensing cap further comprises:

said cylindrical shaped body including a cylindrical shaped wall that extends from the proximal end to the distal end of said cylindrical shaped body; and said internal dividing wall located inside said cylindrical shaped body that divides said cylindrical shaped body into two parts, wherein said internal dividing wall extends between the proximal end of said cylindrical shaped body and the inner surface of said distal end wall for dividing the inner surface of said distal end wall into a first region that is in fluid communication with the distal end of said first lumen through the first radial opening and a second region that is in fluid communication with the distal end of said second lumen through the second radial opening.

21. The spray tip as claimed in claim 20, further comprising:
a first fluid pathway formed in the first region of the inner surface of said distal end wall of said dispensing cap, wherein said first fluid pathway is located between the distal end of said first lumen and said first spray orifice; and
a second fluid pathway formed in the second region of the inner surface of said distal end wall of said dispensing cap, wherein said second fluid pathway is located between the distal end of said second lumen and said second spray orifice.

22. The spray tip as claimed in claim 21, wherein said first fluid pathway comprises a first swirl chamber formed in the inner surface of said distal end wall that is in fluid communication with said first spray orifice, and a pair of first flutes that are formed in the inner surface of said distal end wall and that extend radially outward from said first swirl chamber, and wherein said second fluid pathway comprises a second swirl chamber formed in the inner surface of said distal end wall that is in fluid communication with said second spray orifice, and a pair of second flutes that are formed in the inner surface of said distal end wall and that extend radially outward from said first swirl chamber,
wherein said first flutes extend from an inner surface of said cylindrical shaped body to an outer perimeter of said first swirl chamber, and wherein said second flutes extend from the inner surface of said cylindrical shaped body to an outer perimeter of said second swirl chamber.

\* \* \* \* \*